(12) United States Patent
Limem et al.

(10) Patent No.: US 10,058,417 B2
(45) Date of Patent: *Aug. 28, 2018

(54) ABSORBABLE IMPLANTS FOR PLASTIC SURGERY

(71) Applicant: Tepha, Inc., Lexington, MA (US)

(72) Inventors: Skander Limem, Melrose, MA (US); Emily Stires, Cambridge, MA (US); Rebecca Holmes, North Reading, MA (US); Said Rizk, Windham, NH (US); Arikha Moses, New York, NY (US); Fabio Felix, Foxborough, MA (US); Bruce Van Natta, Westfield, IN (US); Antonio Fosco, North Reading, MA (US); David P. Martin, Arlington, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,330

(22) Filed: Apr. 17, 2017

(65) Prior Publication Data

US 2017/0216018 A1 Aug. 3, 2017

Related U.S. Application Data

(63) Continuation of application No. 14/694,681, filed on Apr. 23, 2015, now Pat. No. 9,655,715, which is a (Continued)

(51) Int. Cl.
*A61F 2/12* (2006.01)
*A61F 2/00* (2006.01)
(Continued)

(52) U.S. Cl.
CPC .............. *A61F 2/12* (2013.01); *A61F 2/0063* (2013.01); *A61F 2210/0004* (2013.01);
(Continued)

(58) Field of Classification Search
CPC ........................................................ A61F 2/12
(Continued)

(56) References Cited

U.S. PATENT DOCUMENTS 4,801,299 A * 1/1989 Brendel .............. A61L 27/3633
128/DIG. 8
5,011,494 A * 4/1991 von Recum .......... A61F 2/0077
600/36
(Continued)

FOREIGN PATENT DOCUMENTS

WO 2004096098 11/2004
WO 2006117622 11/2006
(Continued)

OTHER PUBLICATIONS

Auclair and Mitz, "Repair of mammary ptosis by insertion of an internal absorbable support and periareolar scar", Ann. Chir. Plast. Esthet. 38:107-13 (1993).
(Continued)

*Primary Examiner* — Suzette J Gherbi
(74) *Attorney, Agent, or Firm* — Pabst Patent Group LLP

(57) ABSTRACT

Absorbable implants for breast surgery that conform to the breast parenchyma and surrounding chest wall have been developed. These implants support newly lifted breast parenchyma, and/or a breast implant. The implants have mechanical properties sufficient to support a reconstructed breast, and allow the in-growth of tissue into the implant as it degrades. The implants have a strength retention profile allowing the support of the breast to be transitioned from the implant to regenerated host tissue, without significant loss of (Continued)

support. Three-dimensional implants for use in minimally invasive mastopexy/breast reconstruction procedures are also described, that confer shape to a patient's breast. These implants are self-reinforced, can be temporarily deformed, implanted in a suitably dissected tissue plane, and resume their preformed three-dimensional shape. The implants are preferably made from poly-4-hydroxybutyrate (P4HB) and copolymers thereof. The implants have suture pullout strengths that can resist the mechanical loads exerted on the reconstructed breast.

20 Claims, 13 Drawing Sheets

Related U.S. Application Data continuation-in-part of application No. 14/329,760, filed on Jul. 11, 2014, now Pat. No. 9,532,867.

(60) Provisional application No. 61/845,236, filed on Jul. 11, 2013, provisional application No. 61/993,511, filed on May 15, 2014.

(51) Int. Cl.
  B29C 47/00    (2006.01)
  B29L 31/00    (2006.01)
  B29K 67/00    (2006.01)

(52) U.S. Cl.
  CPC ............ *A61F 2210/0014* (2013.01); *A61F 2210/0061* (2013.01); *A61F 2230/008* (2013.01); *A61F 2230/0076* (2013.01); *A61F 2240/001* (2013.01); *B29C 47/004* (2013.01); *B29C 47/0014* (2013.01); *B29C 47/0066* (2013.01); *B29K 2067/04* (2013.01); *B29K 2995/006* (2013.01); *B29L 2031/7532* (2013.01)

(58) Field of Classification Search
  USPC ........................................................ 623/7–8
  See application file for complete search history.

(56) References Cited

U.S. PATENT DOCUMENTS

| | | | | |
|---|---|---|---|---|
| 5,658,329 | A * | 8/1997 | Purkait | A61F 2/12 623/23.72 |
| 6,210,439 | B1 | 4/2001 | Firmin | |
| 7,476,249 | B2 | 1/2009 | Frank | |
| 7,670,372 | B2 | 3/2010 | Shfaram | |
| 7,998,202 | B2 * | 8/2011 | Lesh | A61F 2/0059 623/11.11 |
| 8,034,270 | B2 | 10/2011 | Martin | |
| 9,532,867 | B2 * | 1/2017 | Felix | B29C 47/08 |
| 9,636,211 | B2 * | 5/2017 | Felix | B29C 47/08 |
| 9,655,715 | B2 * | 5/2017 | Limem | A61F 2/12 |
| 2008/0027273 | A1 | 1/2008 | Gutterman | |
| 2008/0097601 | A1 | 4/2008 | Codori-Hurff | |
| 2009/0082864 | A1 | 3/2009 | Chen | |
| 2010/0191330 | A1 | 7/2010 | Lauryssen | |
| 2010/0217388 | A1 * | 8/2010 | Cohen | A61F 2/0059 623/8 |
| 2010/0249947 | A1 * | 9/2010 | Lesh | A61L 27/16 623/23.74 |
| 2010/0331612 | A1 | 12/2010 | Lashinski | |
| 2012/0022646 | A1 | 1/2012 | Mortarino | |
| 2012/0185041 | A1 | 7/2012 | Mortarino | |
| 2012/0226352 | A1 | 9/2012 | Becker | A61F 2/12 623/8 |
| 2012/0283826 | A1 | 11/2012 | Moses | |
| 2014/0017284 | A1 * | 1/2014 | Yang | A61F 2/02 424/400 |
| 2014/0046442 | A1 | 2/2014 | Guterman | A61F 2/12 623/8 |
| 2014/0135925 | A1 | 5/2014 | Brooks | A61F 2/12 623/8 |
| 2014/0163696 | A1 * | 6/2014 | Lesh | A61L 27/16 623/23.74 |
| 2014/0222146 | A1 | 8/2014 | Moses | A61F 2/12 623/8 |
| 2014/0257482 | A1 * | 9/2014 | Ward | A61F 2/0059 623/8 |
| 2014/0276993 | A1 | 9/2014 | Reilly | D04C 1/06 606/151 |
| 2015/0018946 | A1 | 1/2015 | Guterman | A61F 2/12 623/8 |
| 2015/0351889 | A1 | 12/2015 | Reddy | A61F 2/0063 606/151 |
| 2015/0351891 | A1 | 12/2015 | Moses | A61F 2/12 623/8 |
| 2015/0351899 | A1 | 12/2015 | Mortarino | A61F 2/12 623/8 |
| 2016/0038269 | A1 * | 2/2016 | Altman | A61F 2/0059 623/8 |

FOREIGN PATENT DOCUMENTS

| | | |
|---|---|---|
| WO | 2009001293 | 12/2008 |
| WO | 2011119742 | 9/2011 |
| WO | 2012122215 | 9/2012 |

OTHER PUBLICATIONS

De Bruijn, et al., "Mastopexy with mesh reinforcement: the mechanical characteristics of polyester mesh in the female breast", Plast. Reconstr. Surg. 124:364-71 (2009).
Goes, "Periareolar memmaplasty: double-skin technique with application of mesh support", Clin. Plast. Surg., 29:349-64 (2002).
Goes, "Periareolar mammaplasty: double skin technique with application of polyglactine or mixed mesh", Plast. Reconstr. Surg,. 97:959-68 (1996).
Goes and Bates, "Periareolar mastopexy with FortaPerm", Aesth. Plast. Surg., 34:350-8 (2010).
International Search Report and Written Opinion for PCT/US2014/046420 dated Oct. 22, 2014.
Johnson, "Central core reduction mammoplasties and Marlex suspension of breast tissue", Aesth. Plast. Surg. 5:77-84 (1981).
Van Deventer, et al., "Improving the longevity and results of mastopexy and breast reduction procedures: reconstructing an Internal breast support system with biocompatible mesh to replace the supporting function of the ligamentous suspension", Aesth. Plast. Surg. 36:578-89 (2012).
Williams, et al., "Poly-4-hydroxybutyrate (P4HB): a new generation of resorbable medical devices for tissue repair and regeneration", Biomed. Tech., 58(5):439-52 (2013).

* cited by examiner

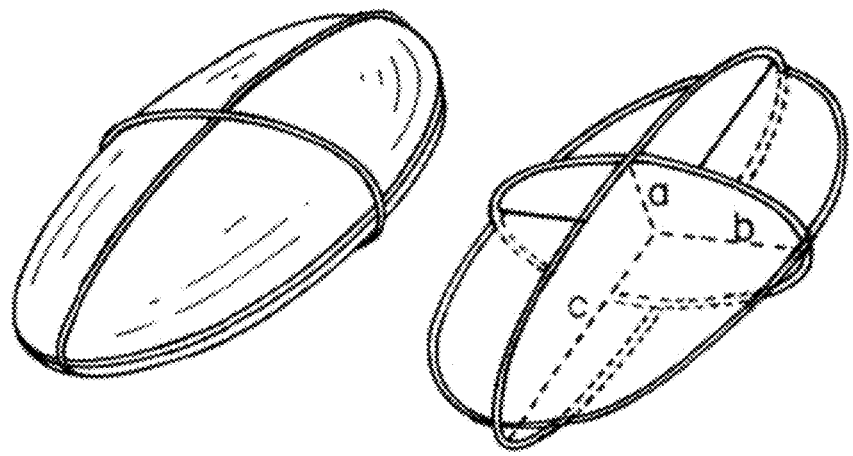
FIG. 4A  FIG. 4B
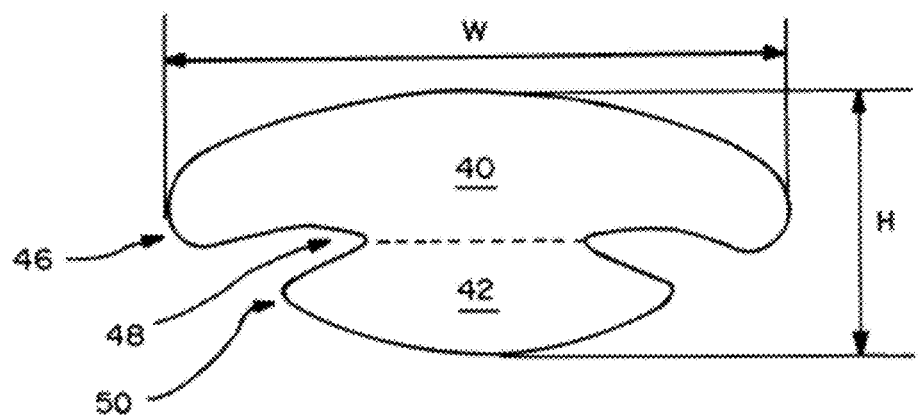
FIG. 5

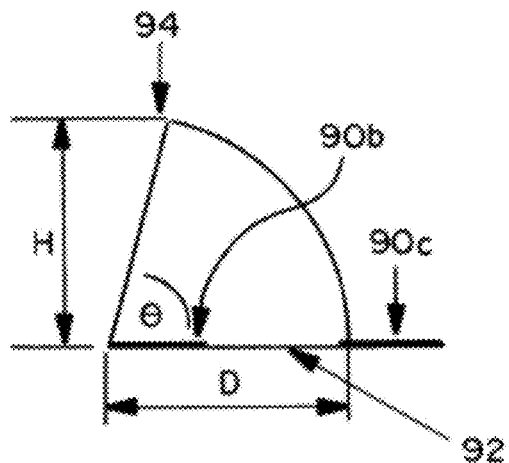
FIG. 11D
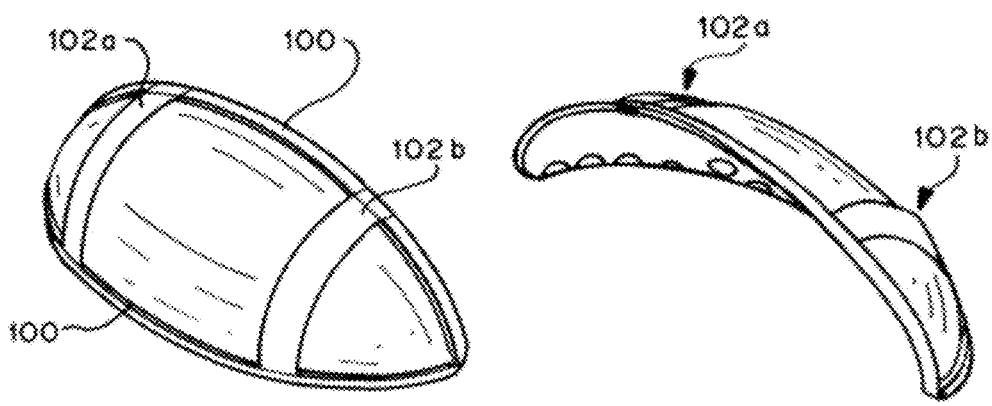
FIG. 12A
FIG. 12B

ABSORBABLE IMPLANTS FOR PLASTIC SURGERY

CROSS-REFERENCE TO RELATED APPLICATIONS

This application is a continuation of U.S. Ser. No. 14/694,681, filed Apr. 23, 2015, which is a continuation-in-part of U.S. Ser. No. 14/329,760, filed Jul. 11, 2014, which claims the benefit of and priority to U.S. Ser. No. 61/993,511 filed May 15, 2014 and U.S. Ser. No. 61/845,236, filed Jul. 11, 2013, all of which are incorporated by reference in their entirety.

FIELD OF THE INVENTION

The present invention generally relates to absorbable implants that are shaped or have shaped memory so they can conform to anatomical structures or confer shape to anatomical structures, and are designed for use in plastic surgery procedures.

BACKGROUND OF THE INVENTION

Numerous plastic surgery procedures are performed each year to restore or correct the form or function of the body. Many of these procedures seek to restore a youthful appearance, or even to enhance one's existing appearance. Natural factors, such as aging and gravity, contribute to the loss of the youthful appearance. For example, skin laxity, loss of muscle tone, and attenuation of ligaments can result in ptosis (drooping) of the breast. Plastic surgeons have developed a plethora of surgical techniques to correct the ptosis of different anatomical structures that occurs with aging. These techniques vary in the type of incision, direction of incision, plane of dissection, amount of dissection, extent of repositioning of tissue, the use of different types of sutures, different suturing techniques, and different fixation techniques. Almost all of them rely on the use of the pre-existing skin envelope as the support system for the newly lifted tissue. These approaches almost invariably result in recurrent ptosis, since the surgeon is merely relying on the aging and sagging surrounding tissues that have already failed to provide the necessary support to maintain a normal appearance. For example, de-epithelialization, flap transposition, gland repositioning or suturing will not alter the physical properties of the patient's tissue. At most, these techniques only slow recurrent ptosis by creating internal scars that provide limited reinforcement. And even the scarring process varies from patient to patient making this limited approach highly unpredictable. Notably, there is no attempt with these approaches to change the physical properties of the local tissue in order to improve the outcome.

Several surgeons have attempted to reinforce their lift procedures using surgical meshes in mastopexy and breast reconstruction procedures. Some of these techniques have also incorporated the use of various reinforcing materials similar to those used in hernia repair, such as flat polymeric meshes, allografts, xenografts and autografts.

In 1981, Johnson described the use of MARLEX® (crystalline polypropylene) mesh to convert the support of breast tissue after mastopexy from a cutaneous origin to a skeletal origin by attaching the mesh to the area of the second rib, (Johnson, *Aesth. Plast. Surg.* 5:77-84 (1981)). The flat MARLEX® mesh is a permanent mesh made from polypropylene, and was implanted to provide two slings in each breast that supported the breast tissue. It is not replaced with regenerated host tissue.

Auclair and Mitz have described a mesh assisted mastopexy using a flat absorbable mesh and a periareolar skin resection technique (Auclair and Mitz, *Ann. Chir. Plast. Esthét.* 38:107-113 (1993)). A rapidly absorbing VICRYL® mesh was placed around the anterior surface of the breast gland in order to form an internal bra.

Góes has reported the use of polyglactin 910 (an absorbable copolymer of 90% glycolide and 10% L-lactide, also known as VICRYL®) and a mixed mesh (containing 60% polyglactine 910 and 40% permanent polyester) in a periareolar mammoplasty using a double skin technique (Góes, *Plast. Reconstr. Surg.* 97:959-968 (1996)). The technique involves dissecting the soft tissue envelope away from the parenchyma, and wrapping the breast parenchyma with a mesh to help provoke the formation of a vigorous connective scar to produce a breast lining structure that would be less susceptible to ptosis. The soft tissue envelope is then closed around the parenchyma. In the procedure, a dermal flap was created around the nipple-areolar complex, and after the lift procedure was completed, the dermal flap was sutured on top of the breast gland to provide an internal cutaneous lining. The mesh was then sutured on top of the dermal flap so that it surrounded the breast gland, and the ends of the mesh were sutured together in the central part of the superior aspect of the breast to form a conical breast shape with slight elevation of the breast. Although the mesh was found to provide short-term support, it was absorbed after 3 months. Better results were reported with the mixed (partially absorbable) mesh. The latter provided a less elastic envelope, avoided tissue displacement, and improved the quality and duration of the new breast shape (Sampaio Góes, *Clin. Plast. Surg.* 29:349-64 (2002)).

U.S. Pat. No. 6,210,439 to Firmin et al. discloses a circular VICRYL® mesh with a V-shaped opening extending from its center that has a metallic reinforcing wire running around the periphery. The implant assumes a conical shape suitable for mammoplasty when the reinforcing wire is tightened. However, VICRYL® mesh degrades rapidly in vivo with 50% loss of strength retention at five days, no residual strength at 10-14 days, and complete absorption at 42 days. This strength retention profile provides very little time for the formation of regenerated host tissue that can withstand the forces exerted on the breast. In fact, Góes and Bates concluded "absorbable synthetic meshes do not persist sufficiently to have an impact on the recurrence of breast ptosis" [see Góes and Bates, Periareolar mastopexy with FortaPerm, *Aesth. Plast. Surg.* 34:350-358 (2010)].

WO 2009/001293 by de Bruijn et al. also discloses permanent mesh implants for use in mesh assisted mastopexy (see also de Bruijn et al., *Aesth. Plast. Surg.* 32:757-765 (2008)). These implants were performed in the shape of oblique circular cones with the apex removed so that they could be placed all the way around the entire breast gland with the nipple-areolar complex remaining exposed (effectively making an internal bra). The cones were made from two different non-degradable materials, polypropylene and a permanent polyester material. The results obtained with the softer polyester cone implants were considered to be superior to those achieved with the more rigid polypropylene implants. In the latter case, rippling of the polypropylene mesh in some patients resulted in a less than satisfactory appearance, the margins of the mesh were often palpable, and in some cases extrusion of the mesh occurred. Examination of the polyester mesh removed from a patient in pain was reported to show that the mesh appeared to possess the proper mechanical characteristics necessary to reinforce a ptotic breast during mastopexy (de Bruijn et al., *Plast. Reconstr. Surg.* 124:364-71 (2009)).

Van Deventer et al. has also reported the use of an internal breast support system for mastopexy using a partially degradable mesh that was formed into a cone by overlapping the ends of the mesh (van Deventer et al. *Aesth. Plast. Surg.* 36:578-89 (2012)). The mesh contained 50% polypropylene and 50% absorbable polyglactin.

A permanent implant for soft tissue support, made from polytetrafluoroethylene (ePTFE), which can be used in forming a predetermined breast shape is disclosed by WO 2004/096098 by Hamilton et al. WO 2006/117622 by Lauryssen et al. also discloses a permanent implant for soft tissue support of the breast that is generally L-shaped or U-shaped, but is made from polypropylene.

U.S. Pat. No. 7,476,249 to Frank discloses an implantable sling shaped prosthesis device for supporting and positioning a breast implant in a patient, wherein the device is configured from a sheet of a chemically inert permanent material, such as polytetrafluoroethylene or silicone, to support the breast implant. The sling shaped device provides support to the breast but does not have shape memory that allows it to confer shape to the breast or retain a three-dimensional shape.

U.S. Patent Application Publication No. 2009/0082864 by Chen et al. also discloses a prosthetic device for supporting a breast implant made from a mesh. The device has a flat back wall, a concave front wall, and a curved transitional region between these walls that forms a smoothly curved bottom periphery.

U.S. Pat. No. 7,670,372 to Shfaram et al. discloses a minimally invasive breast lifting system. The system incorporates a biological material, such as tendons, or synthetic material, such as silicone or GOR-TEX® material (polytetrafluoroethylene), to cradle the breast.

U.S. Patent Application Publication No. 2012/0283826 by Moses et al. discloses mastopexy systems having an insertion device, a suspension strut, and a lower pole support. The implanted suspension strut provides pole projection and attachment points for the lower pole support, and the lower pole support can lift the lower pole of the breast.

U.S. Patent Application Publication No. 2008/0097601 by Codori-Hurff et al. discloses mastopexy and breast reconstruction procedures assisted by the use of processed tissue material derived from intestine or dermis. The tissue material is cut to a crescent shape, and may have up to 10 layers bonded together. The bonded layers can be chemically cross-linked.

U.S. Patent Application Publication No. 2008/0027273 by Gutterman discloses a minimally invasive mastopexy system having a soft tissue support sling. The latter can be made from polyethylene, PEBAX® (polyether block amide), PEEK (polyether ether ketone), nylon, PET (polyethylene terephthalate), ePTFE (polytetrafluoroethylene), silicone, or even a metal lattice. The device is designed to provide support by suspending the breast from the upper pole region using a bone anchor. The device does not have shape memory, and does not use shape memory to confer shape to the breast.

U.S. Patent Application Publication No. 2010/0331612 by Lashinski et al. discloses a system for performing a minimally invasive mastopexy (breast lift) that can include an elongate flexible sling used as a soft tissue anchor. The sling can be made from a mesh, and the mesh can be made, for example, from polypropylene. The sling is designed to resist weakening or degradation when implanted.

Notably, there is very little innovation in the design of flat meshes that when implanted can provide a specific conformation to the inferior support envelope without bunching or rippling. The problems associated with permanent mesh could be overcome by using an absorbable implant that is replaced with regenerated host tissue capable of supporting the reconstructed breast. Ideally, the absorbable implant would be pre-shaped to ensure a good outcome, and for ease of use. Notably, there are no disclosures of the use of any pre-shaped asymmetric absorbable implants for use in mastopexy or breast reconstruction. Prior disclosures have only described symmetrical two-dimensional shapes, such as ellipse shaped implants, which wrinkle, bunch or fold when the implant is attached to the breast mound and the fascia (see, for example, U.S. Patent Application Publication No. 2008/0097601 by Codori-Hurff et al.), pre-shaped hammocks and slings which are symmetrical three-dimensional shapes that are designed to conform to the lower pole of the breast (see, for example, U.S. Pat. No. 7,476,249 to Frank which discloses an implantable sling), or pre-shaped symmetrical cone shaped implants [de Bruijn et al., *Aesth. Plast. Surg.* 32:757-765 (2008)]. In order to make implants that conform to the anatomy of the breast and anchor to the chest wall, the plastic surgeon needs to trim, cut, or excise material from the implant.

PCT/US2012/027975 by Galatea Corporation discloses mastopexy systems to provide superior pole projection, to prevent ptosis recurrence, which may include tabs to enhance positioning.

U.S. Patent Application Publication No. 20120185041 to Mortarino et al. discloses methods for using silk meshes in breast augmentation and breast reconstruction with a knit pattern that substantially prevents unraveling when cut. Mortarino does not disclose silk meshes with shape memory, asymmetric or three-dimensional shapes. Mortarino also does not disclose meshes with shape memory that confer shape to a breast.

It is therefore an object of the invention to provide scaffold implants strong enough to support a lifted breast with or without a breast implant wherein the scaffold allows a transition from support by the implant to support by regenerated host tissue without any significant loss of support for the breast.

It is another object of the invention to provide implants that have suture pullout strengths strong enough to support the weight of a breast and/or a breast augmented with a breast implant.

It is still another object of the invention to provide implants that have a shape and design that upon placement, substantially conforms to the breast and chest wall without buckling or bunching, and sculpts the breast into the desired shape.

It is yet another object of the invention to provide shape memory implants for use in mastopexy and breast reconstruction procedures that can be temporarily deformed, and have the ability to spring open into a three-dimensional shape after delivery into a suitably shaped tissue plane of the body.

It is still further an object of the invention to provide shape memory implants for use in mastopexy and breast reconstruction procedures that confer shape on the breast, and can take the shape of the lower pole of the breast, and implants that are self-reinforced so they possess shape memory and can open into three-dimensional shapes.

SUMMARY OF THE INVENTION

Absorbable implants for use in breast surgery that are designed to conform to the breast parenchyma and surrounding chest wall have been developed. These implants are designed to support newly lifted breast parenchyma, and/or a silicone breast implant. The implants have initial mechanical properties sufficient to support a breast, with or without a breast implant, and allow the in-growth of tissue into the implant as the implant degrades. The implants also have a strength retention profile that allows the support of the breast to be transitioned from the implant to regenerated host tissue without any significant loss of support for the reconstructed breast. The implants can be made from poly-4-hydroxybutyrate (P4HB) and copolymers thereof. The implants have suture pullout strengths that can resist the mechanical loads exerted on the breast.

In one embodiment, the implants have a shape that: is conformable to the breast and chest wall without causing buckling or bunching; minimizing the need to trim the implant during surgery; and sculpturing the breast into the desired shape.

Absorbable implants are also disclosed with shape memory. These shape memory implants can be temporarily deformed, and can be delivered by minimally invasive techniques for mastopexy and breast reconstruction procedures. The implants can resume their preformed shapes after delivery into a suitably shaped tissue plane in the body. The shaped memory implants can confer a shape to the breast. In a preferred embodiment, the absorbable implants have an asymmetric shape.

BRIEF DESCRIPTION OF THE DRAWINGS

FIG. 4A is a diagram of a hemi-ellipsoid implant shape. FIG. 4B is a schematic of the implant with the cross-section dimensions of its three-dimensional shape defined by tri-axial dimensions "a", "b" and "c".

FIG. 5 is a diagram of an implant for breast reconstruction with a wide upper span (40) to facilitate sling support and encompass the breast mound, and an extra-large bottom tab (42) to support the breast vertical pillar and shape the inframammary fold (IMF), rounded corners (46) and deep in cuts (48). The two-dimensional implant shape is designed to minimize bunching or folding of the implant during breast reconstruction.

FIG. 10A shows a partial dome shape of the implant, that is designed to contour and add shape to the breast mound. FIG. 10B shows the width (W) of the partial dome, and (80) shows the arch or edge of the dome viewed looking inside the dome. FIG. 10C shows the height (H), depth (D), and angle (θ) between the base (or floor) (84) of the partial dome and the edge (82) of the partial dome at its highest point (86).

FIG. 11A shows a three-dimensional partial dome shaped implant (90) with three tabs (90a, 90b, 90c) for breast reconstruction that is designed to contour and add shape to the breast mound. FIG. 11B shows the width (W) of the partial dome and placement of the tabs (90a, 90b, 90c). FIG. 11C shows the view of the implant looking from above the partial dome. FIG. 11D shows the height (H), depth (D), and angle (θ) between the base (or floor) (92) of the partial dome and the edge of the partial dome at its highest point (94).

FIG. 12A shows an example of how a three-dimensional partial dome shaped implant, viewed from above, can be reinforced with body ribbing (100) around the edge and body ribbing (102) in the mid-dome region (102a and 102b) of the implant. FIG. 12B shows the same three-dimensional implant as FIG. 12A, except viewed from above and looking partially inside the dome.

DETAILED DESCRIPTION OF THE INVENTION

Figure 1:
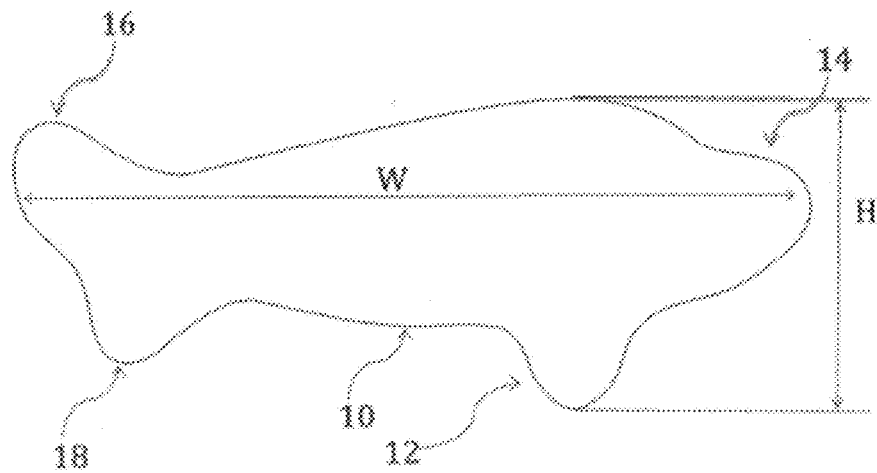
FIG. 1 is a diagram of an asymmetric implant (10) for breast reconstruction with a teardrop shape and additional tabs (12, 14, 16, 18).

Ideally, it would be preferable to use an absorbable implant for mastopexy and other breast reconstruction procedures that has a longer strength retention profile, and the demonstrated ability to regenerate healthy host tissue to support the breast. Such regenerated host tissue could replace or reinforce the ligamentous suspension system of the breast, acting as an artificial suspensory, and release the skin from the function of maintaining breast shape. The use of a prolonged strength retention absorbable implant to provide an even suspension of the breast instead of using sutures would also eliminate the formation of linear stress lines associated with suture only breast lift techniques, as well as eliminate the time required to adjust sutures to optimize appearance. It would also be desirable to use minimally invasive techniques in mastopexy and breast reconstruction procedures to implant these absorbable implants.

Furthermore, it would be desirable to provide the surgeon with a fully pre-shaped implant with shape memory and/or self-expansion capability that can be temporarily deformed to allow for implantation, and then resume its original preformed three-dimensional shape after placement in a suitably dissected tissue plane. The implant may be inserted in a folded, crimped, or constrained conformation. After insertion in a suitably shaped tissue plane, the implant would spring or open back into an opened conformation of its own volition and due to its inherent design. This procedure would be somewhat analogous in technique to a standard breast augmentation procedure, wherein a small (1 to 3 inch) incision is created at the inframammary fold (IMF). This incision is merely used by the surgeon as an access point through which the surgeon dissects a much larger tissue plane into which the implant is placed by deforming the implant and pushing it through the (small) incision.

It should be noted that such shape memory implants would differ substantially from other implants previously disclosed for breast lift and reconstruction procedures. First, these shape memory implants would have the ability to be temporarily deformed, and then to open or spring into a shape after they are delivered in vivo into a suitably shaped tissue plane. This property eliminates the need for the surgeon to unroll, for example, a flat mesh after implantation in vivo, and remove wrinkles in the mesh, and also further enables minimally invasive procedures. Second, the shape memory implants would be designed to confer shape to the breast unlike other implants previously disclosed that must be shaped or draped around the breast. Third, the shape memory implants are not suspension devices that are suspended from the upper pole region by, for example, sutures. Fourth, the shape memory implants are self-reinforced to allow the implants to spring into shape or deploy into an open conformation once implanted in vivo.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Bicomponent" as generally used herein means a structure containing two or more materials.

"Blend" as generally used herein means a physical combination of different polymers, as opposed to a copolymer formed of two or more different monomers.

"Burst pressure" as used herein is determined according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Copolymers of poly-4-hydroxybutyrate" as generally used herein means any polymer containing 4-hydroxybutyrate with one or more different hydroxy acid units.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Shape Memory" as used herein describes a property of the implant that allows the user to squeeze, pull, roll up, fold up, or otherwise deform the implant temporarily in order to facilitate its insertion in the body wherein the device recovers its preformed shape after insertion in the body.

"Self-reinforced" as used herein describes a property of the implant in which the outer rim is strengthened such that the implant can be squeezed, pulled, rolled, folded, or otherwise temporarily deformed by the user to facilitate its insertion in the body, and that allows the implant to recover its initial shape after insertion in the body.

"Split metal form" is used herein interchangeably with "split metal mold".

"Support rib" is used herein interchangeably with "ribbing" and "ring" to refer to reinforcement around the edge of the implant.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Taber Stiffness Unit" is defined as the bending moment of ⅕ of a gram applied to a 1½" (3.81 cm) wide specimen at a 5 centimeter test length, flexing it to an angle of 15°, and is measured using a Taber V-5 Stiffness Tester Model 150-B or 150-E. The TABER® V-5 Stiffness Tester—Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 0.0981 milliNewton meters (mN m). Taber Stiffness Units can be converted to Genuine Gurley™ Stiffness Units with the equation: $S_T = 0.01419 S_G - 0.935$, where $S_T$ is the stiffness in Taber Stiffness Units and $S_G$ is the stiffness in Gurley Stiffness Units. To convert Taber Stiffness Units to Millinewton Meters, use the equation: $X = S_T \cdot 0.098067$, where X is the stiffness in Millinewton Meters.

II. Implants

Poly-4-hydroxybutyrate (P4HB, TephaFLEX® biomaterial) is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water.

U.S. Pat. No. 8,034,270 to Martin et al. discloses methods for making combination devices of P4HB with autologous, allogenic and/or xenogenic tissues for use in mastopexy and breast reconstruction, among other applications. WO 2011/119742 by Martin et al. discloses PHA monofilament and multifilament fibers coated with spin finish, and devices derived therefrom, including breast reconstruction devices. There is no disclosure of specific designs for use in these procedures, nor properties of these devices that are necessary to regenerate host tissue strong enough to support the breast and prevent recurrent ptosis. There is also no disclosure of shape memory designs, and designs that allow the implant to confer shape on the breast. Moreover, there is no disclosure of implants that retain a three-dimensional shape irrespective of whether the implant is placed in contact with a three-dimensional part of the anatomy.

Figure 14A:
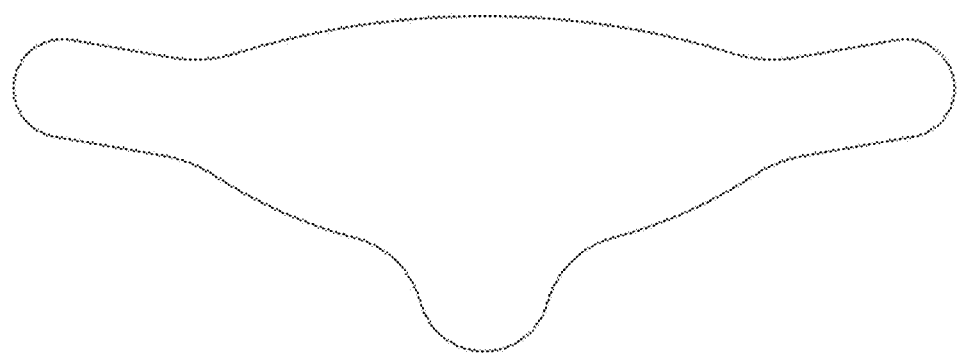
FIG. 14A shows a custom die to cut mesh and ribbing to size and create 3 fixation tabs.
Figure 14B:
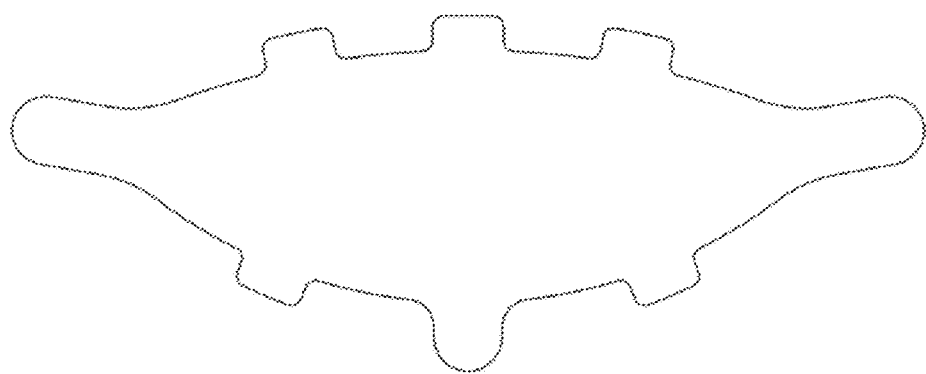
FIG. 14B shows custom die to cut mesh and ribbing to size and create 8 fixation tabs.
Figure 14C:
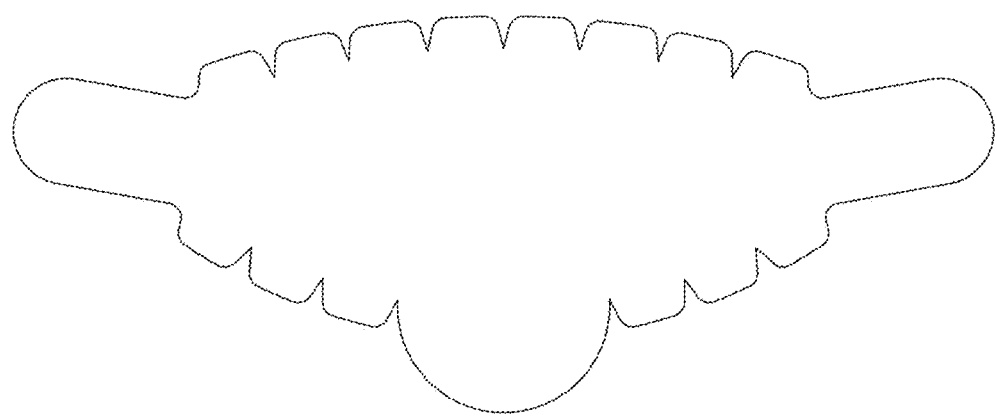
FIG. 14C shows custom die to cut mesh and ribbing to size and create 17 fixation tabs.
Figure 14D:
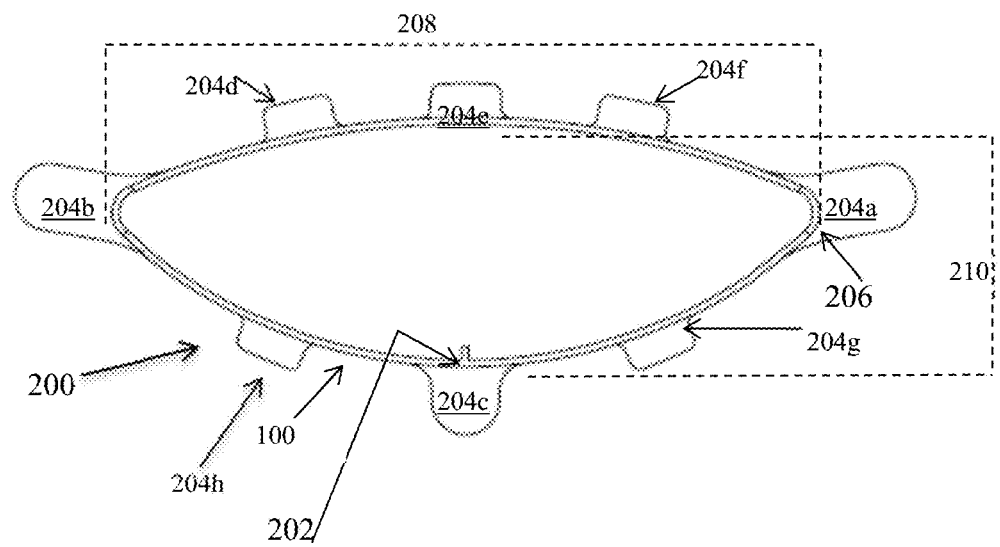
FIG. 14D shows flat view of a three dimensional partial dome mesh implant (200) with eight fixation tabs (204a to 204h) and a uniform perimeter support ribbing (100) made from P4HB extrudate, showing an upper section with an M-L distance (208) which is a measure of the width of the device, an IMF-NAC (Nipple Areolar Complex) NAC distance (210) which is a measure of the height of the device, an orientation mark (202) located in the lower section of the device, a lateral tab (204a), a medial tab (204b), an IMF central tab (204c), additional tabs (204d, 204e, 204f, 204g and 204h) and a rounded edge (206) to reduce stress in the implant.

Referring to FIG. 14D, the implants have a three dimensional shape and include a scaffold which has an upper section a lower section, medial side, lateral side, and an outlying border.

In order to prevent recurrent breast ptosis and aid in shaping the breast parenchyma during a mastopexy or reduction procedure, implants made of P4HB or other materials should have strength retention times longer than one to two months that over time can be replaced with regenerated host tissue, and that are able to support the lifted breast mound/parenchyma (including withstanding the forces exerted by any breast implant). The implant should: (i) have mechanical properties sufficient to support the breast, and any breast implant, while regenerated host tissue develops; (ii) allow predictable tissue in-growth as the implant slowly loses strength and is absorbed; (iii) have a strength retention profile that allows a transition from support by the implant to support by regenerated host tissue without any significant loss of support; (iv) have a shape and design that (a) is conformable to the breast and chest wall without buckling or bunching, (b) has sufficient suture pullout strength to resist the mechanical loads exerted on the reconstructed breast, (c) minimizes the need to trim the implant during surgery, and (d) sculpts the breast into the desired shape; (v) optionally possess shape memory so that it can be temporarily deformed to allow for implantation and resume its original preformed three-dimensional shape essentially unaided; (vi) optionally have a 3-dimensional shape that substantially represents the shape of the lower pole of the breast, and (vii) optionally confer a shape to the breast.

Absorbable implants have been developed that are comprised of scaffolds, which over time can be replaced with regenerated host tissue that is able to support a surgically revised breast (including withstanding the forces exerted by any breast implant). The implants are preferably made from poly-4-hydroxybutyrate or copolymer thereof. PHA fibers can be converted into meshes and slings for breast reconstruction that allow some fibrous tissue ingrowth, and yet are soft, supple, and barely palpable once implanted.

The implants disclosed herein have mechanical properties that are sufficient to support the load of the breast, and the additional load of any breast implant, while regenerated host tissue develops. Following implantation, the implant scaffold structure allows a predictable in-growth of tissue as the implant slowly loses strength and is absorbed. The scaffold has a prolonged strength retention profile to ensure a smooth transition from support of the breast by the implant to support of the breast by regenerated host tissue without any significant loss of support. As such, the implant can maintain the ideal shape of the operated breast that was assembled during surgery.

A major advantage of these implants over existing mesh assisted breast surgery and specifically mastopexy is that a regenerated tissue that is strong enough to prevent recurrent ptosis replaces the implants. This eliminates the problems and concerns associated with the use of permanent or partially absorbable meshes, such as contraction, long-term chronic inflammatory and foreign body response and allows for long-term changes in breast volume that can result from pregnancy and weight gain or loss. The disclosed implants have major advantages over prior approaches that have used absorbable polygalactin 910 (VICRYL®) meshes. The latter meshes undergo very rapid loss of strength in vivo, and are completely absorbed in about 42 days. This rapid absorption process provides little time for a regenerated host tissue to form that can support the load on the breast. In contrast, the P4HB implants have a prolonged strength retention profile, and in a preferred embodiment can maintain some residual strength for as much as one year. The prolonged presence of these implants provides an extended period for tissue ingrowth into their scaffold structures, and a residual strength to prevent early recurrent ptosis while the regenerated tissue forms. Importantly, the in-grown tissue provides strength and support beyond the time of complete strength loss of the implant, thus demonstrating the implant's ability to provide a durable repair beyond its absorption timeframe.

In an embodiment, the absorbable implants are designed so that when manufactured, they are flat; however, when placed around a breast, they have a shape that conforms to the contours of the breast and chest wall without causing any buckling or bunching of the implant or tissue structures. The implants are designed to help sculpt the breast into the desired profile, and shaped to minimize the need to trim the implants during surgery. In a particularly preferred embodiment, the implants are asymmetric. In contrast, absorbable meshes used in existing approaches have generally been symmetric in shape. In a preferred embodiment, the asymmetric shaped implants are made from poly-4-hydroxybutyrate or copolymer thereof.

In another embodiment, the implants are designed to have suture pullout strengths high enough to resist the initial mechanical loads exerted by the breast, and to maintain sufficient pullout strength while tissue in-growth occurs. In contrast, polyglactin 910 (VICRYL®) rapidly loses strength, and has negligible suture pullout strength after just a few days.

In a yet another embodiment, the implants are preformed three-dimensional shapes with shape memory, designed to actively provide shape to the lower pole of the breast parenchyma. The implants can be temporarily deformed and resume their original preformed shapes after implantation into a suitably dissected tissue plane. The implants may aid in conferring a shape to the breast, and are self-reinforced. In a preferred embodiment, the three-dimensional shaped implants with shape memory are made from poly-4-hydroxybutyrate or copolymer thereof.

In another preferred embodiment, the implant has a three-dimensional shape and shape memory properties that allow it to assume its original three-dimensional shape unaided after it has been delivered through a small incision and into an appropriately sized dissected tissue plane. For example, the implant may be temporarily deformed by rolling it up into a small diameter cylindrical shape, delivered using an inserter, and then allowed to resume its original three-dimensional shape unaided in vivo. In addition, the implant may be squeezed in between the fingers to shorten the distance between the two furthest points of the implant in order to facilitate its delivery through an incision smaller than the width of the device.

A. Properties of the Implants i. Mechanical Properties

The absorbable implants have been designed to support the mechanical forces acting on the breast during normal activities at the time of implantation, and to allow a steady transition of mechanical forces to regenerated host tissues that can also support those same mechanical forces once the implant has degraded. Design of the implant includes selection of the absorbable material, and its form (such as mesh, film, foam), degree of orientation, and molecular weight. This will also determine factors such as surface area and porosity. At rest, the load exerted on a large breast weighing, for example, 1 kg, is 9.8 Newtons (N). During exercise where vertical acceleration can reach 2-3 g, or in extreme exercise peak at around 6 g, the force on the breast could rise to nearly 60 N. In a preferred embodiment, the absorbable implants can withstand a load of at least 5 N, more preferably of at least 15 N, and even more preferably of at least 60 N.

Since the implants are absorbable, it is beneficial that the implants be replaced with regenerated host tissue strong enough to support the breast. In some embodiments, it is beneficial that the implants contain a porous scaffold that can allow tissue in-growth, and the formation of a regenerated tissue strong enough to support the breast after the implant is degraded and absorbed. In an embodiment, the scaffold structure of the implant has pore diameters that are at least 50 µm, more preferably at least 100 µm, and most preferably over 250 µm.

When the implant scaffold has been completely replaced by regenerated host tissue, it must be able to support the breast. The force per area that the regenerated tissue needs to be able to withstand to prevent recurrent ptosis depends upon the size of the reconstructed breast, activity level of the patient, and any additional force exerted by a breast implant. In an embodiment, the regenerated tissue supporting the reconstructed breast can withstand a pressure of at least 0.1 kPa, more preferably at least 1 kPa, and even more preferably at least 5 kPa. In an even more preferred embodiment, the combination of the implant and the regenerating tissue forming in the implant scaffold can also withstand a pressure of at least 0.1 kPa, more preferably at least 1 kPa, and even more preferably at least 5 kPa.

In a particularly preferred embodiment, the absorbable implants are sutured in place. This means that although in theory the load exerted by the breast is spread out over the implant, the entire force of the breast tissue is shared among the points of attachment of the implant to the body. A major advantage is that the absorbable implants disclosed herein possess a high suture pullout strength that allows a heavy breast to be supported with a limited number of anchoring sites. The high suture pullout strength can be obtained for example, as a result of selection of the absorbable material, molecular weight, orientation, form (such as monofilament mesh or film), and porosity.

In a preferred embodiment, a P4HB implant is anchored to the chest wall at four or more places in order to support the breast. This strategy distributes the load over multiple attachment points. In a particularly preferred embodiment, the suture pullout strength of the absorbable implant is greater than 10 N, and more preferably greater than 20 N.

The implant can be designed either so that it stretches equally in each direction, or it may stretch more in some directions than in other directions. The ability of the implant to stretch can allow the surgeon to place tension on the breast during implantation. However, in order to maintain support for the breast following surgery, it is critical that after the implant is implanted, the implant, the regenerated host tissue, and any transitional structures, cannot stretch significantly. In an embodiment, the implant cannot stretch more than 30% of its original length in any direction. In an even more preferred embodiment, the implants cannot stretch more than 30% of their original length in any direction and are made from poly-4-hydroxybutyrate or copolymer thereof. This property is imparted on the implant for example as a result of the degree of orientation of the absorbable material, and also the weave or knit pattern if it is a textile.

It is particularly important that the surgeon is able to contour the implant to the surface of the breast parenchyma or breast implant. It is also desirable that the implant is not palpable through the skin once implanted. The implants have been designed so that they are pliable, yet can remodel with increased in-plane stiffness over time to keep the breast in the desired shape. In a preferred embodiment, the implants are compliant and have a Taber stiffness that is less than 100 Taber Stiffness Units, more preferably less than 10 Taber Stiffness Units, and even more preferably less than 1 Taber Stiffness Unit. The intrinsic property of the absorbable material, degree of orientation and relaxation of the polymer imparts on the implant the desired Taber Stiffness.

In a particularly preferred embodiment, the implant has properties that allow it to be delivered through a small incision. The implant may, for example, be designed so that it can be rolled or folded to allow delivery through a small incision. This minimally invasive approach can reduce patient morbidity, scarring and the chance of infection.

ii. Tabs and Retainers

The implants can incorporate one or more tabs to accommodate suture throws or other anchoring devices for the fixation of the implant to the patient's tissues. These tabs can be placed in order to improve the implant's ability to conform and shape to the breast, as well as to adapt to the chest wall. In particular, these tabs can be incorporated with appropriate spacing into the implant so that they amplify the implant's ability to bend and stretch around the lower curvature (lower pole) of the breast without causing bunching, kinking, folding or wrinkling of the implant. The width of the tabs can range from 1 cm to 3 cm and the length from 2 to 4 cm and can range in number from 1 to 20. For example, the implants can have 2, 3, 4, 5, 6, 7, 8, 9, 10, 11, 12, 13, 14, 15, 16, 17, 18, 19 or 20 tabs. Referring to FIG. 14D, the implant can include three tabs (204e, 204d and 204f) in the upper section, three tabs 204c, 204h and 204g in the lower section, one tab 204b in the medial section and one tab 204a in the lateral section of the device.

In another embodiment, the implants comprise retainers, such as barbs or tacks, so that the implant can be anchored to the chest wall without the use of additional suture. For example, the three-dimensional implants may contain retainers in their outlying borders to anchor the implants.

iii. Reinforced Rim

Figure 14E:
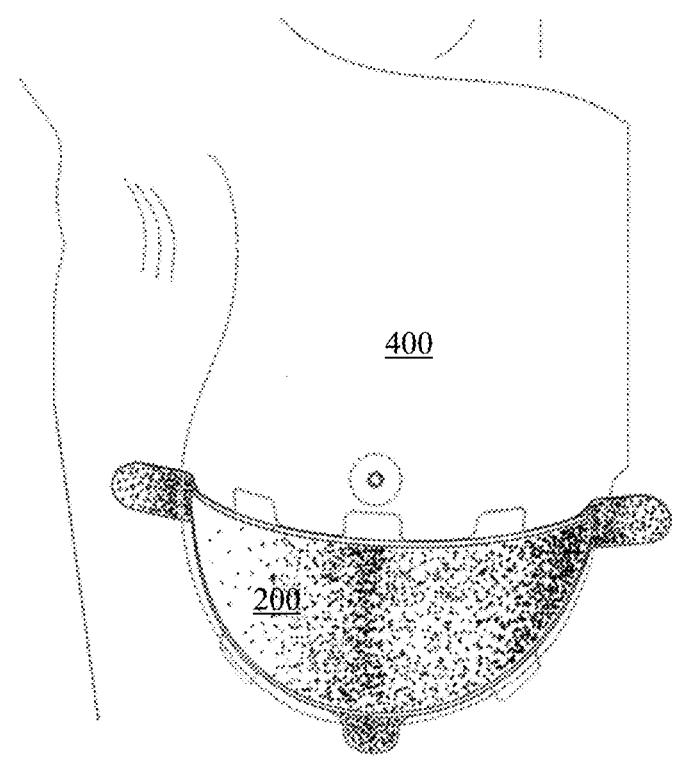
FIG. 14E shows the device 200, placed on a breast 400.

The rim of the implants is preferably resorbable and reinforced. In some embodiments, the rim has an offset elliptical (American football) shape. In this embodiment, top and bottom half of the rim are composed of circular arcs with collinear centers (FIG. 14E). The upper section can have a curvature range from 10-15 cm, and the lower section can have a curvature range from 21-25.5 cm. The arcs can be designed so that the ratio of their curvature radii follows the golden ratio rule described in section iv.2a (Three-dimensional shaped implants). In some preferred embodiments, the rim has rounded edges. Rounded edges help to eliminate stresses in the implant. The rim edge radius can be for example, 0.6 cm for a small sized implant, 0.7 cm for a medium sized implant and 0.8 cm for a large sized implant.

The outer rim of the implant can be strengthened with a ring/ribbing. For example, the outlying border can be reinforced by a continuous or interrupted ring of: filament, thread, strand, string, fiber, yarn, wire, film, tape, tube, fabric, felt, mesh, multifilament, or monofilament. In a preferred embodiment, the implant is formed from a monofilament mesh with an outlying border reinforced by a continuous ring of monofilament, preferably, a P4HB monofilament. To minimize palpability after implantation while performing the functions above, the rim is made out of a resorbable material with diameter not exceeding 2.0 mm.

To help reduce the amount of material used to make the rim while delivering the stiffness needed for maintaining the 3D shape, the rim can be designed using a decreasing (negative gradient) diameter from the IMF-central position towards the medial and lateral edges.

Ribbing around the edge of the implant that can be either one-sided or two sided and/or with a profile that changes. The support rib can be included along the perimeter of the implant or in the mid dome of the implant, continuously or intermittently (interrupted) for example, a number of ribbing lengths shorter than the perimeter of the device, can be placed intermittently along the perimeter of the device. The number of ribs and spacing used for interrupted placement can be selected as desired. The rib can be of uniform cross-sectional radius or it can have decreasing cross-sectional radius (i.e., a profile that changes).

Figure 13A:
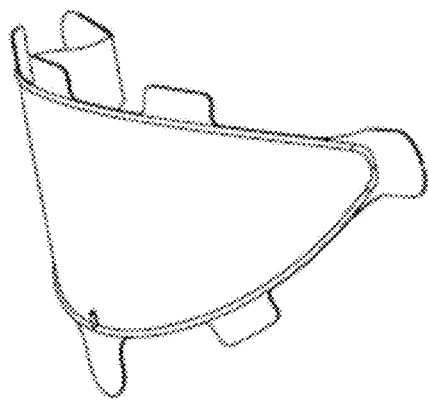
FIG. 13A shows unidirectional curvature for a 3D implant.
Figure 13B:
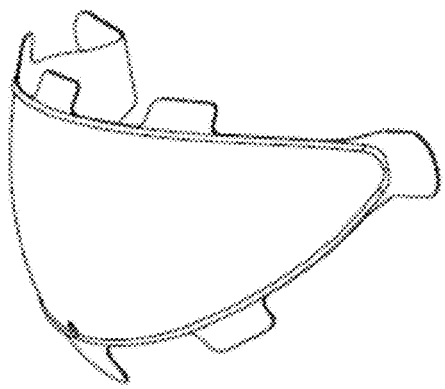
FIG. 13B shows bidirectional curvature for a 3D implant.
Figure 13C:
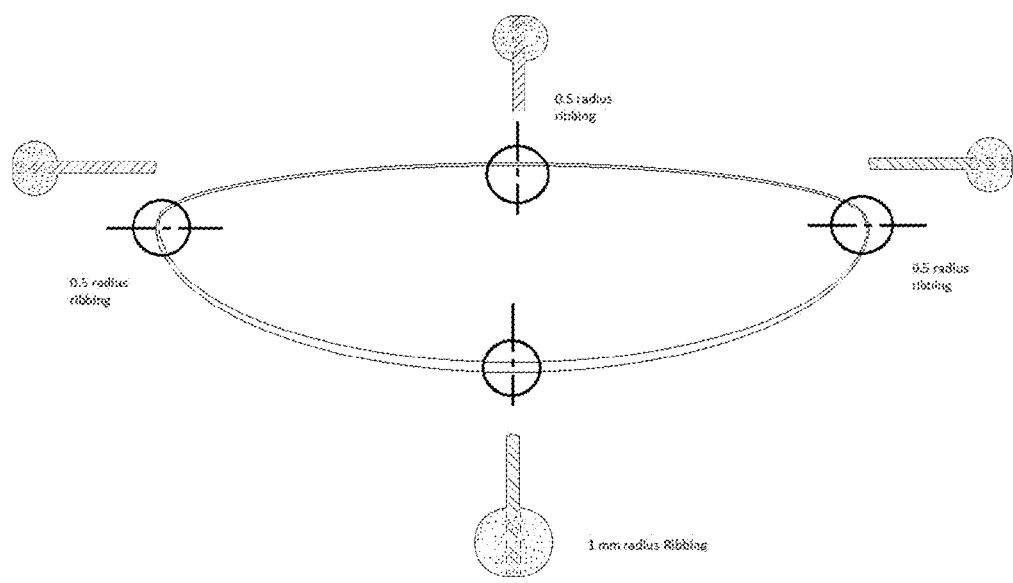
FIG. 13C shows perimeter support ribbing with decreasing radius of the ribbing.

An example of an implant with a three-dimensional partial dome shape that has been reinforced with ribbing is shown in FIG. 12, FIGS. 13C and 14D. In FIG. 12, the partial dome shaped implant is reinforced with a continuous body ribbing along the perimeter (100 of the dome and in the mid-dome (102a and 102b) section. An example of an implant with a three-dimensional partial dome shape that has been reinforced with a continuous ribbing of decreasing cross-sectional radius is shown in FIG. 13C.

iv. Shapes

The implants can be prepared in sizes large enough to allow for their use in mastopexy and other breast reconstruction procedures such that they are wide enough to substantially span the width of a breast, and for the surgeon to cut and trim the implants, if and as necessary, to the required sizes and shapes. In one embodiment, the implants are cut and shaped so that they can be used in a mastopexy procedure (with or without a breast implant) or in any other breast reconstruction procedure. In a preferred embodiment, the implants are pre-cut and shaped so that they will conform to the anatomical shape of the reconstructed breast. In another embodiment, the implants can be cut and shaped to reinforce breast tissues, and in particular so that there is no buckling or bunching of the implant. In still another embodiment, the implants are two-dimensional (i.e. flat), but can be formed around three-dimensional shapes without any buckling or bunching of the implant.

In yet another embodiment, the implants are designed so that they can help to sculpt breast parenchyma into the desired shape. In a particularly preferred embodiment, the implants have anatomical shapes, three-dimensional shapes, and/or asymmetric shapes. These shapes minimize the need to cut or trim the implant during use, and also minimize any buckling or bunching of the implant.

Non-limiting examples of a support include a mesh, a set of strips, a fabric, a woven construct, a non-woven construct, a knitted construct, a braided construct, a porous scaffold, a porous film including laminated and perforated film, a nanospun, electrospun, or melt-blown construct.

The implants may be shaped into an anatomical shape, two-dimensional shape, three-dimensional shape, and/or asymmetric shape, minimizing any buckling or bunching of the implant upon placement.

The implants combine various features to optimize mechanical properties. For example, various combinations of implant body shapes, tab shapes, tab locations, number of tabs, thickness of body, type of material, and material processing result in increased mechanical properties including but not limited to increased suture pull out strength, increased breast load, increased stiffness, and increased load after several months (e.g. increased load after 78 weeks).

1. Asymmetric Implants

In one embodiment shown in FIG. 1, a body 10 of the asymmetric implant is shaped into a teardrop. This shape helps to prevent the implant from buckling or bunching, minimizes the need to cut or shape the implant during surgery, provides a low profile to avoid coverage of the nipple-areolar complex, and facilitates sculpturing the breast to create enhanced cleavage. Tabs 12, 14, 16, 18 or other shapes can also protrude from the teardrop, for example, to accommodate suture throws or other anchoring devices, maximize load distributions, and further shape the contours of the reconstructed breast. These tabs also allow the implant to contour tightly to the breast mound without forming wrinkles or folds. In a preferred embodiment, the width to height ratio of the teardrop ranges from a ratio of 10:1 to 1.5:1, and is more preferably 5:2. For example, the width (W) of the teardrop implant (shown in FIG. 1) can be about 25 cm and the height (H) of the teardrop shown in FIG. 1) can be 10-11 cm as. (The width of the teardrop is the longest distance measured between any two points, and the height of the teardrop is the longest distance measured perpendicular to the width.)

With reference to FIG. 1, four tabs are shown extending from body 10. Two tabs 12, 14 are shown extending from a base or wider portion of the teardrop, and an additional two tabs 16, 18 are shown extending from the narrow or tip portion of the tear drop. The tabs are shown in an asymmetric arrangement. Tabs assist with contouring to the breast tissue, and providing a platform for fastening the implant to tissue. Although four tabs are shown in FIG. 1, the body 10 may include more or less than four tabs. Preferably, the implant includes at least 4 tabs.

The implant may be installed in either breast. The implant shown in FIG. 1 is suited for a mastopexy procedure.

In a particularly preferred embodiment, the teardrop can incorporate seam lines that can be embossed to project the two-dimensional structure of the implant into a three-dimensional structure that accentuates the breast contouring.

Figure 2:
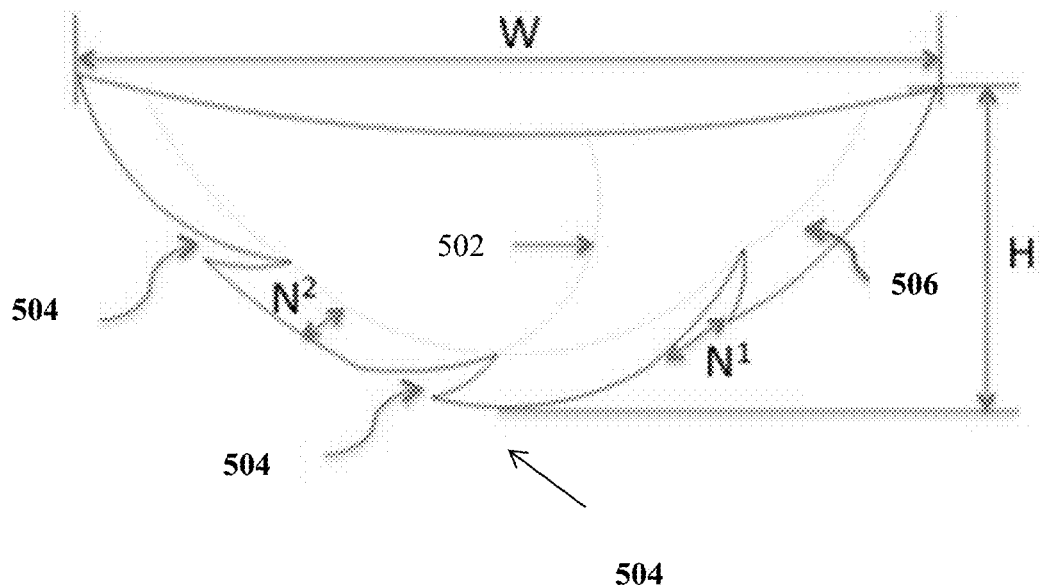
FIG. 2 shows a diagram of an asymmetric two-dimensional implant (500) for use in reconstruction of the right breast with a width (W), height (H), a mid-body curved support (502), cut notches (504) and tabs (506) to allow the implant to stretch over the breast mound without bunching.

In another embodiment, the asymmetric implant is shaped as shown in FIG. 2, and used to reconstruct a right breast. An implant with a shape that is the mirror image of FIG. 2 may be used to reconstruct a left breast. The implant optionally has a curved mid-body support (90) to improve breast mound contouring and support, cut notches (92) and tabs (94) to minimize stress concentrations and allow the implant to stretch over the breast mound with minimal bunching. The notched sections may, if desired, be stitched closed to create a three-dimensional cup shape. In an embodiment, the implant has a width (W) between 22 and 30 cm, a height (H) between 7.5 and 11 cm, a perimeter notch gap ($N^1$) between 0.5 and 4 cm, and a tab width ($N^2$) between 1 and 2 cm.

When the shape of the three-dimensional implant is substantially a hemi-ellipsoid, the dimensions of the implant may be defined by the tri-axial dimensions "a", "b" and "c" shown in FIGS. 4A and 4B. In a preferred embodiment, the ranges of these dimensions are preferably "a" from 2 to 10 cm, "b" from 3 to 10 cm, and "c" from 2.5 to 12 cm.

2. Shaped Implants

One embodiment of a two-dimensional implant is shown in FIG. 5. The upper region (40) of the implant has a larger footprint than the lower region (or tab) (46) of the implant, and is designed to support the breast parenchyma by spreading the load to key anchoring points. The implant features deep in cuts (48) that allow the lower region (or tab) (42) to fold at the IMF (i.e. at the dashed line in FIG. 7) and give shape to the IMF without bunching of the implant. The implant shown in FIG. 5 also incorporates rounded corners (e.g. (46)) to eliminate stress concentrations in the implant. In a preferred embodiment, the width (W) of the implant shown in FIG. 5 is between 18 cm and 36 cm, and the height (H) of the implant is between 6 cm and 14 cm.

Figure 6:
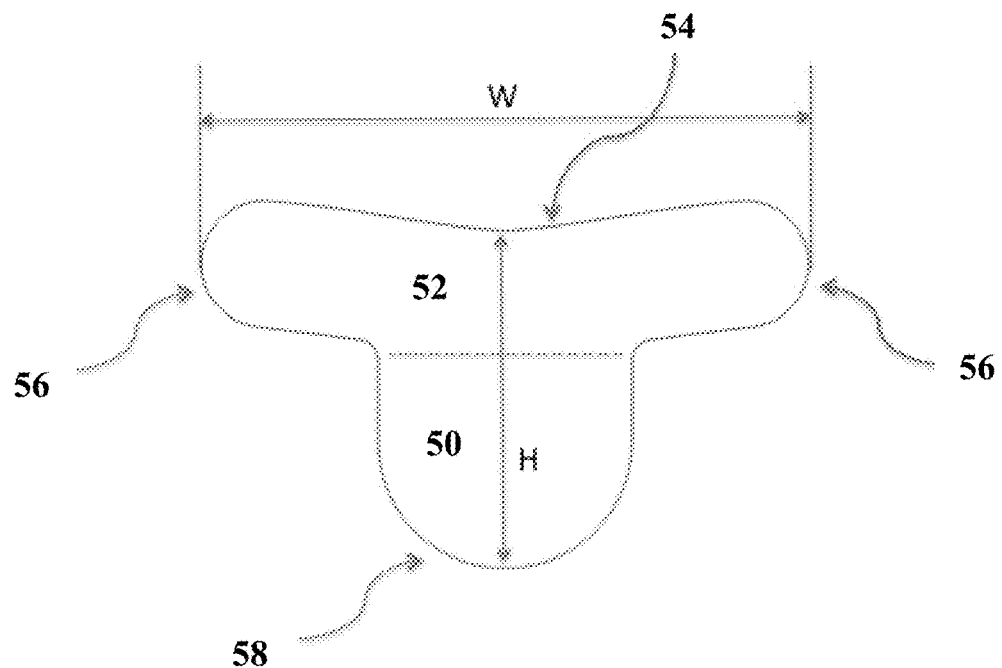
FIG. 6 is a diagram of a two-dimensional implant for breast reconstruction designed to support the breast mound that features a curved upper line (54) in the upper region (52) to improve breast mound conformity, a short right to left span to anchor the scaffold to the breast mound, rounded corners (56) and (58), an upper and an oblong lower tab (50) with rounded corners to support the vertical pillar or fold under the IMF to provide shape and support to the breast.

Another embodiment of a two-dimensional implant is shown in FIG. 6. The upper region (52) of the implant also has a larger footprint than the lower region (or tab) (50) of the implant, and is also designed to support the breast parenchyma by spreading the load to key anchoring points. Instead of incorporating deep in cuts, the implant has a curved upper line (54) to allow the implant to conform and support the breast parenchyma without the implant bunching. The implant shown in FIG. 6 also incorporates rounded corners (56) and (58) to eliminate stresses in the implant. An oblong-shaped tab (50) allows the implant to fold at the IMF (i.e. at the dashed line in FIG. 6) and give shape to the IMF and support to the vertical pillar. In contrast to the implant shown in FIG. 5, the implant shown in FIG. 6 has a shorter width or span from left to right to anchor the implant on the breast mound. In a preferred embodiment, the width (W) of the implant shown in FIG. 6 is between 10 cm and 26 cm, and the height (H) of the implant is between 6 cm and 14 cm.

Figure 7:
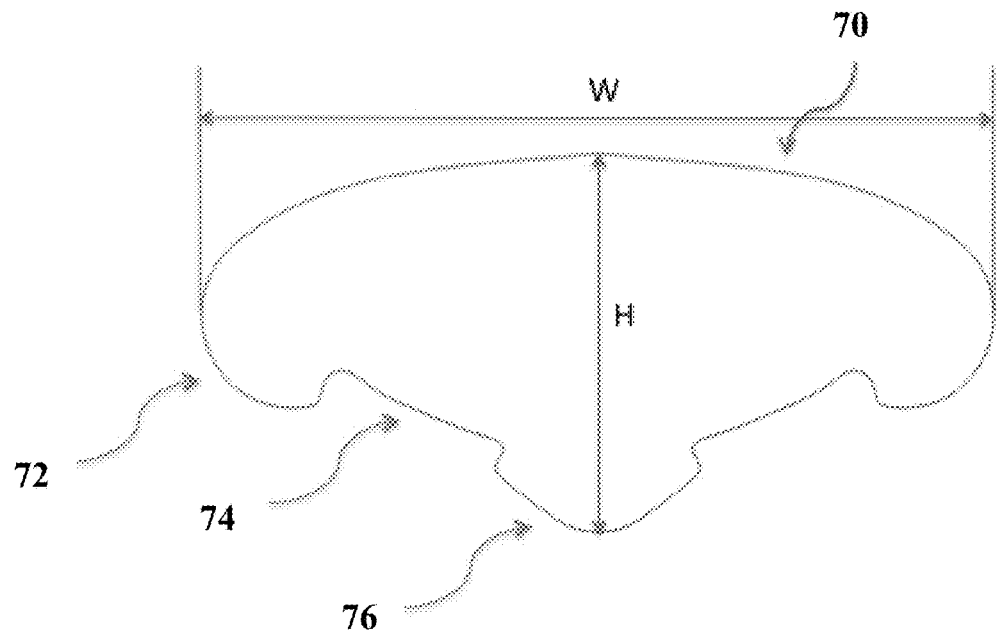
FIG. 7 is a diagram of an implant for breast reconstruction designed to support the breast mound and distribute the load to specific anchoring positions. The two-dimensional implant features a curved upper line (70) which provides a wide right to left curved span to provide sling support defined by width "W", and insets (74) between anchor tabs (72 and 76) on the lower side to conform to the shape of the IMF without bunching of the implant.

A further embodiment of the two-dimensional implant is shown in FIG. 7. The implant has a curved upper line (70) (like the implant of FIG. 6) to allow the implant to conform to the breast without bunching, and a wide left to right span (like the implant of FIG. 5) to facilitate sling support of the breast parenchyma. The implant has a bottom tab (76) to anchor the implant and support the breast vertical pillar, and side tabs (e.g. (72)) separated from the bottom tab (76) with inset cuts to allow the implant to flex between tabs and form a curved IMF. The implant also features rounded corners to eliminate stress concentrations in the implant. In a preferred embodiment, the width (W) of the implant shown in FIG. 7 is between 18 cm and 34 cm, and the height (H) of the implant is between 8 cm and 16 cm.

The implants may also be crescent-shaped, rectangular or any other shape. As a crescent shape, the implant can transition from a first low profile or rolled configuration to a deployed shape. The implant can also be a canoe-like body including walls and a cavity formed therein. The cavity serves to accommodate the breast parenchyma when deployed. The implant can be configured as a sheet, a solid sheet, or as a discontinuous layer such as a mesh.

Figure 8:
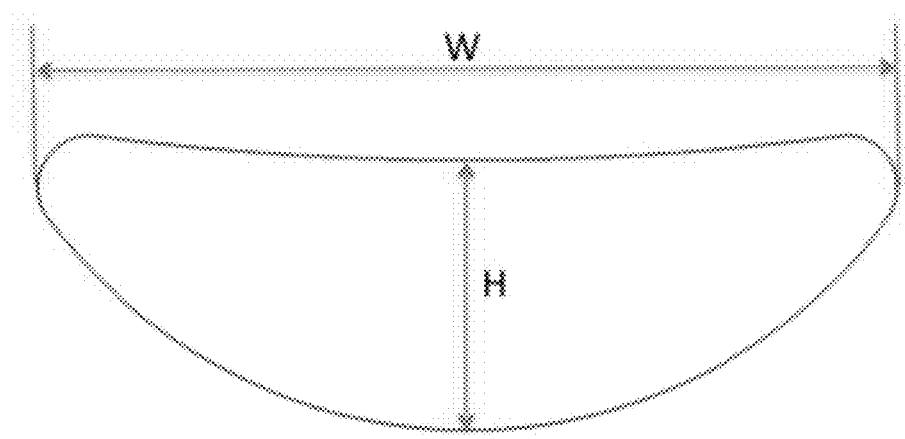
FIG. 8 shows an example of a two-dimensional crescent shaped implant with a width (W) and height (H).

An example of a crescent shaped implant is shown in FIG. 8. In a preferred embodiment, the crescent shaped implant has a width (W) of 10 to 25.5 cm, and a height (H) of 5 to 11 cm.

Figure 9:
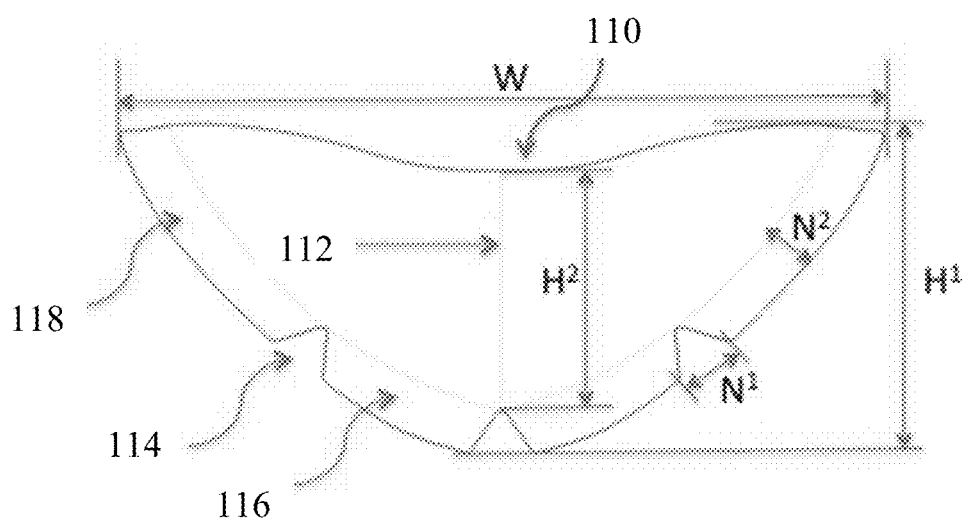
FIG. 9 shows a diagram of a two-dimensional implant for breast reconstruction of width (W) and height ($H^1$) with a recess (110) for the nipple areola complex, an option for mid-body support (112), and tabs (116) and (118) to allow the implant to stretch over the breast mound without bunching.

Another example of an implant with an upper curving profile is shown in FIG. 9. The two-dimensional implant incorporates a recess (110) for the nipple areola complex (NAC), an option for mid-body support (112), and notches (114) that create tabs (116) and (118) so that the implant can be stretched over the breast mound without bunching of the implant. The notched sections may also be stitched closed to create a three-dimensional cup shape. The mid-body support (112) may be stitched or embossed to create a hinge or crease. In an embodiment, the implant (900) has a width (W) between 22 and 30 cm, a height ($H^1$) between 8.5 and 13 cm, a height ($H^2$) between 6.5 and 11 cm, a perimeter notch gap ($N^1$) between 0.5 and 4 cm, and a tab width ($N^2$) between 1 and 2 cm.

a. Three-Dimensional Shaped Implants

The disclosed implants include embodiments with a three-dimensional shape that is designed to provide additional predetermined contour to the host's breast tissue or an anatomical structure of the breast. The implants can have unidirectional or bidirectional curvature. For example, the implant can be designed with two characteristic radii or curvatures: a medial-lateral (M-L) curvature in the M-L plane (See FIG. 13A) and an IMF-Nipple Areolar Complex NAC curvature in the IMF-NAC plane (FIGS. 13B, and 14E). Preferably, the IMF-NAC curvature is less pronounced than M-L curvature, i.e. wider radius. In a preferred embodiment, the curvature for the M-L curvature ranges from 7.5 to 10 cm, and for the IMF-NAC, it ranges from 11 to 20 cm. The ratio of the M-L curvature radius to that of the IMF-NAC ranges is preferably selected to range between 1.5 (=3/2) and 2 (=2/1). The most preferred ratio should be close to 1.61 (golden ratio) to which the ratio of consecutive numbers of the Fibonacci series converges.

Figure 10A:
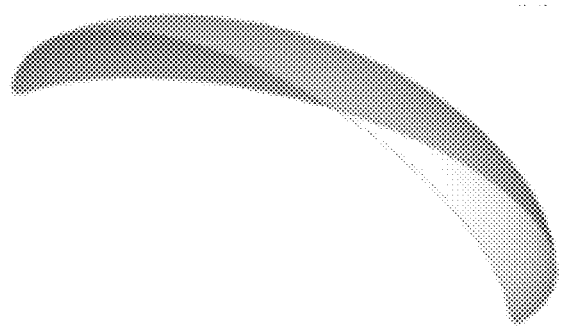
FIGS. 10A to 10C show diagrams of a three-dimensional implant for breast reconstruction.
Figure 10B:
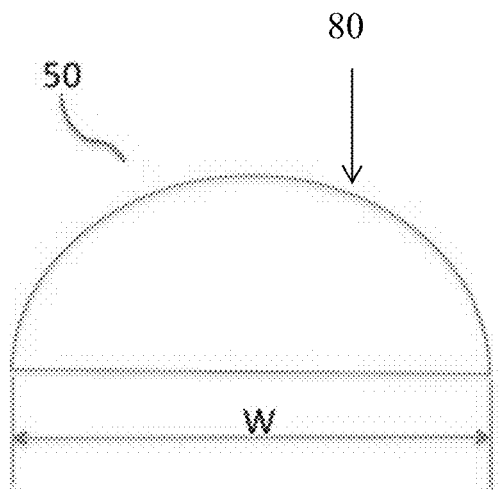
Figure 10C:
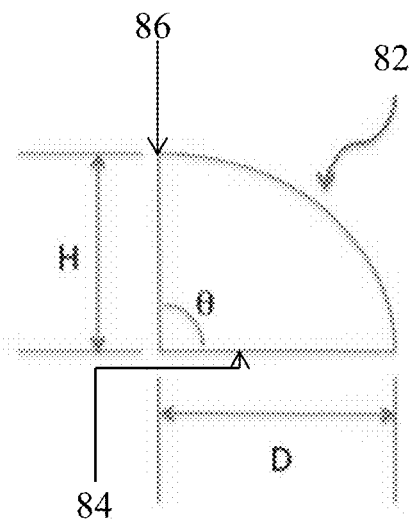

In an embodiment shown in FIG. 10, the implant has a three-dimensional partial dome shape (i.e. FIG. 10A) that allows the implant to capture, contour, and support the breast parenchyma, and distribute the load to key anchoring positions. The ability of the implant to capture and contour the breast parenchyma (i.e. the 3D implant mates and molds with the 3D breast mound) reduces surgery time. In common with the implants of FIGS. 5 and 6, the implants of FIGS. 10A-C, 13C and 14D have rounded corners to eliminate stress concentrations in the implant and prevent bunching of the implant. In a preferred embodiment, the width (W) of the implant shown in FIG. 10B is between 12 and 24 cm, the height (H) measured from the floor or base (84) of the dome to the highest point (86) shown in FIG. 10C is between 2 and 10 cm, and the depth (D) of the dome shown in FIG. 10C is between 2.5 cm and 10 cm. The angle θ shown in FIG. 10C is preferably between 30° and 90°.

Figure 11A:
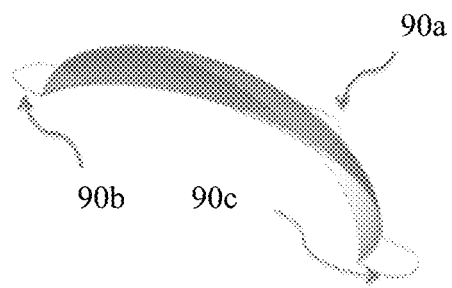
FIGS. 11A to 11C show a three-dimensional dome shaped implant.
Figure 11B:
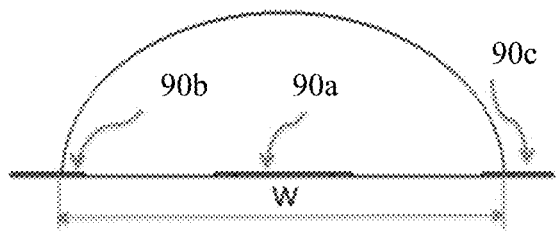
Figure 11C:
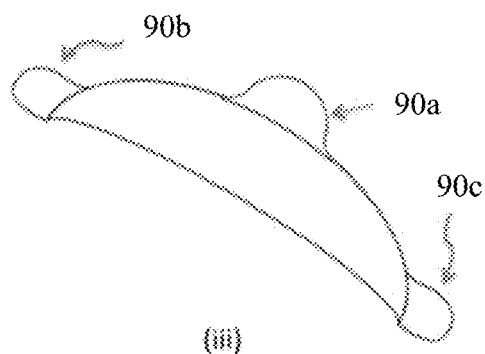

Tabs may be added to the implant shown in FIG. 10A-C, for example, as shown in FIG. 11A-B. The number of tabs can be varied as desired. In the embodiment shown in FIG. 11A, the partial dome implant includes 3 tabs (90a, 90b and 90c), placed at the bottom of the implant (i.e. in the middle, 90a) and at the right and left sides (90b and 90c). Other embodiments show an implant with 8 tabs, which can include an orientation mark for placement (FIG. 14D). In a preferred embodiment, the width (W) of the implant shown in FIGS. 11A-D is between 12 and 24 cm, the height (H) measured from the floor or base of the dome (92) to the highest point (64) shown in FIG. 8D is between 2 and 10 cm, and the depth (D) of the dome shown in FIG. 8D is between 2.5 cm and 10 cm. The angle θ shown in FIG. 8D is preferably between 30° and 90°. Optionally, a support rib can be added to the inner surface of the partial dome implants shown in FIGS. 10 and 11 to provide added support and, if necessary, rigidity, or to add shape retention to the implant (for example, to allow minimally invasive delivery of the implant).

b. Implants with Shape Memory

The three-dimensional shaped implants disclosed herein include implants that have shape memory. The shape memory allows the implant to be temporarily deformed, delivered by a minimally invasive method, and resume its preformed three-dimensional shape once placed across the lower pole of the breast. A particularly preferred three-dimensional shape comprises an outwardly curving exterior, and an inwardly curving interior. An even more preferred three-dimensional shape is self-reinforced and comprises an outwardly curving exterior, an inwardly curving interior, and an outlying border that is reinforced by a continuous or interrupted ring/ribbing described herein. The continuous or interrupted ring allows the implant to assume the desired three-dimensional shape unaided even if the three-dimensional shape has been temporarily deformed, for example, by rolling it into a small diameter cylinder or manipulating it into some other configuration.

The three-dimensional shapes with shape memory may vary in shape and size. Shapes include, but are not limited to, hemispheres, hemi-ellipsoids, domes or similar kinds of shapes. The sizes of the three-dimensional shapes with shape memory vary, and range, for example, from a width of 8 to 20 cm at the base, more preferably 8 to 17 cm at the base, and a height or radius of curvature of 5 to 10 cm. In an embodiment, the width of the three-dimensional shape is designed to be 1 to 2 cm less than the width of the patient's breast after mastopexy. In another embodiment, the height of the three-dimensional shape is 0.5 to 2 cm less than the patient's nipple-IMF distance after mastopexy.

Non-limiting examples of materials that may be used to make these three-dimensional shaped implants with shape memory include meshes (e.g. monofilament and multifilament knitted meshes), strips, fabrics, woven constructs, non-woven constructs, knitted constructs, braided constructs, porous scaffolds, laminates, nanospuns, electrospuns, dry spuns, or melt-blown constructs, filaments, threads, strands, strings, fibers, yarns, wires, films, tapes, felts, multifilaments and monofilaments.

B. Polymers

Any absorbable biocompatible polymer may be used to make the implants provided the implant has sufficient initial strength to shape and support the reconstructed breast, undergoes a controlled resorption process in the breast, and is replaced with regenerated host tissue that can support the breast. The implant may, for example, be prepared from polymers including, but not limited to, polymers of glycolic acid, lactic acid, 1,4-dioxanone, trimethylene carbonate, 3-hydroxybutyric acid, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolactone and copolymers thereof, including random copolymers and block copolymers thereof. Blends of polymers can also be used to prepare the implants. Preferably the polymer or copolymer will be substantially resorbed within a 6 to 18 month timeframe, and retain some residual strength for at least 1-2 months, and more preferably at least 6 months.

In a particularly preferred embodiment, poly-4-hydroxybutyrate (P4HB) or a copolymer thereof is used to make the implant. Copolymers include P4HB with another hydroxyacid, such as 3-hydroxybutyrate, and P4HB with glycolic acid or lactic acid monomer. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for prolonged strength retention.

C. Coatings to Stimulate Cell Attachment and in-Growth

The implants can be coated, derivatized, or modified with other agents in order to improve wettability, water contact angle, cell attachment, tissue in-growth, and tissue maturation.

In one embodiment, the implants can contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

In another embodiment, the implants can incorporate wetting agents designed to improve the wettability of the surfaces of the implant structures to allow fluids to be easily adsorbed onto the implant surfaces, and to promote cell attachment and/or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifyers.

D. Therapeutic, Prophylactic and Diagnostic Agents

The implants may contain bioactive agents.

In a preferred embodiment, the agents improve cell attachment, tissue in-growth, and tissue maturation. The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents.

The bioactive may be proteins such as collagen and antibodies, peptides, polysaccharides such as chitosan, alginate, polysaccharides such as hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

Diagnostic agents include contrast agents, radiopaque markers, or radioactive substances which may be incorporated into the implants.

The implants may also contain allograft material and xenograft materials. In yet another preferred embodiment, the implants may incorporate systems for the controlled release of the therapeutic or prophylactic agents.

II. Methods of Manufacturing Implants

A variety of methods can be used to manufacture the implants, and their scaffold structures. The methods must, however, allow the construction of implants that can: (i) withstand a load of at least 5 N, (ii) support a pressure of at least 0.1 kPa, and (iii) hold a suture with a pullout strength exceeding 10 N. The methods disclosed herein use one or more split metal forms with a semi circular groove, a support component material and a shape memory component material.

The shape memory component material can be selected from a filament, thread, strand, string, fiber, yarn, wire, film, tape, tube, fabric, felt, mesh, multifilament, or monofilament.

The support component material can in some embodiments be porous. Non-limiting examples of a support component materials include a mesh, a set of strips, a fabric, a woven construct, a non-woven construct, a knitted construct, a braided construct, a porous scaffold, a porous film including laminated and perforated film, a nanospun, electrospun, or melt-blown construct. For examples, scaffolds can include fibers, films or non-wovens. The scaffolds can be made using processes such as spinning, molding or 3D printing.

In a preferred embodiment, the method includes the steps of providing a first split metal form with a semicircular groove in one half of the mold; placing a shape memory component material in the semicircular groove so that it forms a ring; placing a support component material between the molding halves, and clamping the two halves of the split metal form together to form a block; heating the block at a temperature between 50° C. and 70° C.; cooling the block at a temperature between 0° C. and 25° C.; disassembling and removing the molded shape from the block; cutting the molded shape to remove unwanted shape memory material and support component material for example, mesh; placing the cut molded shape form in a second split metal form consisting of an inwardly curving half and an outwardly curving half; clamping the halves of the mold together to form a block; heating the block at a temperature between 40° C. and 52° C.; cooling the block at a temperature between 0° C. and 25° C.; disassembling and removing the implant.

A. Method of Making Support Component Materials (i) Porous Scaffolds

In one embodiment, porous scaffolds are prepared using a process that incorporates particulate leaching. This process allows the size and porosity of the scaffold to be controlled by careful selection of the size of the leachable material and its distribution. The scaffolds can be prepared by dispersing particles of the leachable material in a solution of a biocompatible absorbable polymer, wherein the leachable material is not soluble in the polymer solvent. In a preferred embodiment, the leachable particle materials have a diameter of at least 25 µm, and more preferably greater than 50 µm. The leachable particles must be non-toxic, easily leached from the polymer, non-reactive with the polymer, and biocompatible (in case residues are left in the scaffold after leaching). In a preferred embodiment, the leachable particles are water soluble, and can be leached from the polymer solution with water. Examples of suitable particles include salts such as sodium chloride, sodium citrate, and sodium tartrate, proteins such as gelatin, and polysaccharides such as agarose, starch and other sugars. Examples of suitable solvents for the polymers include tetrahydrofuran, dioxane, acetone, chloroform, and methylene chloride. In a particularly preferred embodiment, an implant comprising a porous scaffold is formed from P4HB by adding salt particles (100-180 µm diameter) to a solution of the polymer in dioxanone (10% wt/vol), allowing the solvent to evaporate, pressing the mixture using a hydraulic press with heated platens, and leaching out the salt particles after the polymer has crystallized.

In another embodiment, a process that includes phase separation is used to form the porous scaffold. The size of the pores can be selected by varying parameters such as the solvent, and the concentration of the polymer in the solvent. Suitable solvents include tetrahydrofuran, dioxane, acetone, chloroform, and methylene chloride. In a particularly preferred embodiment, a cast solution of P4HB dissolved in dioxane (3% wt/vol) is frozen at −26° C. to precipitate the polymer, and the solvent sublimated in a lyophilizer to form a phase separated porous P4HB scaffold.

ii. Films

In a further embodiment, the scaffolds can be prepared from films. The films are made by either solvent casting or melt extrusion. The films can be un-oriented, or more preferably oriented in one or more directions so that they have sufficient mechanical properties to support the breast, and provide prolonged strength retention. In order to allow tissue in-growth, the films must be rendered porous or attached to other porous components. Suitable methods for making the films porous include punching or laser drilling holes in the films, or cutting slits or holes in the films. In a particularly preferred embodiment, porous scaffolds are prepared by melt extrusion of P4HB films, and holes are cut, punched or drilled in the films.

iii. Fibers

In still another embodiment, scaffold can comprise thermally bonded fibers. The thermally bonded fibers can be produced by melt extrusion using a multi-holed die. This process allows the diameter of the fibers, the porosity of the scaffold, and the thickness of the scaffold to be controlled by selection of parameters such as the diameter of the die holes, the distance between the die and collector plate, and the collection time. In a preferred embodiment, the thermally bonded fiber scaffold has one or more of the following properties (i) a thickness of 0.1-5 mm, (ii) an areal density or basis weight of 5 to 800 $g/m^2$, (iii) a suture pullout strength of greater than 10 N, and (iv) is able to withstand a pressure of at least 0.1 kPa. In a preferred embodiment, the scaffold is formed from thermally bonded P4HB fibers.

In yet another embodiment, the scaffolds can be prepared from monofilament fibers, multifilament fibers, or a combination of these fibers. Melt extrusion and solution spinning processes can be used to form these fibers. In a preferred embodiment, the scaffolds are woven or knitted from the pre-formed fibers. The scaffolds may be produced by either warp or weft knitting processes, however, a warp knit is preferred in order to minimize the stretching of the scaffold structure. In a preferred embodiment, the scaffold woven from mono or multifilament fibers has one or more of the following properties: (i) stretches less than 30% of the scaffold's original length in any direction, (ii) has a suture pullout strength of at least 10 N, and (iii) can withstand a pressure of at least 0.1 kPa. In a particularly preferred embodiment, the scaffold is made from P4HB monofilament fibers, P4HB multifilament fibers, or a combination of these fibers, and has an areal density of 5 to 800 $g/m^2$. The implant can also be prepared by combining a woven or knitted P4HB construct with a P4HB film.

iv. Non Wovens

The scaffolds can also be formed from structures comprising non-wovens that have been prepared by entangling fibers using mechanical methods. The properties of the nonwovens can be tailored by selection of parameters such as fiber diameter, fiber orientation, and length of the fibers (for staple nonwovens). In a preferred embodiment, the scaffolds comprising non-wovens have one or more of the following properties (i) a thickness of 0.1-5 mm, (ii) an areal density of 5 to 800 $g/m^2$, (iii) a suture pullout strength of greater than 10 N, and (iv) is able to withstand a pressure of at least 0.1 kPa. In a preferred embodiment, the scaffold is formed from a P4HB non-woven.

v. Spinning

The scaffolds may also be formed directly from solution by spinning processes. In these processes, solutions are pumped or forced through dies, and fibers are collected after removal of the polymer solvent. The fiber diameters and porosities of the scaffolds can be controlled by appropriate selection of parameters such as the solvent, temperature, pump pressure or force, die configuration, and the diameter of the holes in the die. In the case of wet spinning, the choice of coagulation non-solvent may be used to control fiber diameter and scaffold porosity and morphology. In a preferred embodiment, the solution spun scaffolds have (i) a thickness of between about 0.5 and 5 mm, (ii) a weight of between 5 and 800 $g/m^2$, (iii) a suture pullout strength of greater than 10 N, and (iv) are able to withstand a pressure of at least 0.1 kPa. In a preferred embodiment, the scaffold is formed from solution spun P4HB fibers.

In still another embodiment, the scaffolds may be prepared by methods that include 3D printing (also known as additive manufacturing). This method is particularly useful in the manufacture of specific shapes since the desired shape can be made directly without the need for further cutting or trimming.

vi. Molding

In still a further embodiment, the scaffolds may be prepared by molding. In these processes, polymer may be directly molded into a scaffold, or the polymer may be first converted into another form (such as a mesh, film, non-woven, laminate, electrospun fabric, foam, thermoform or combinations thereof), and then the form molded, or two methods may be used to form a scaffold that has varying stiffness. In a preferred embodiment, three-dimensional shapes with shape memory are prepared by molding a monofilament mesh into a shape designed to confer shape to the host's breast tissue or form an anatomical shape of the breast. Such shapes include those with an outwardly curving exterior and inwardly curving interior, and optionally contain an outlying border that is reinforced by a continuous or interrupted ring/rib that allows the three-dimensional scaffold to be temporarily deformed and resume a three-dimensional shape. (Such shapes have shape memory.)

The processes described herein to produce the scaffolds can also be used in combination. For example, a woven construct could be combined with a non-woven construct to make a scaffold. In a preferred embodiment, a scaffold can be reinforced with a monofilament or multifilament fiber. In a particularly preferred embodiment, the implants can be reinforced at anchor points to provide, for example, increased suture pullout strength.

Figure 3:
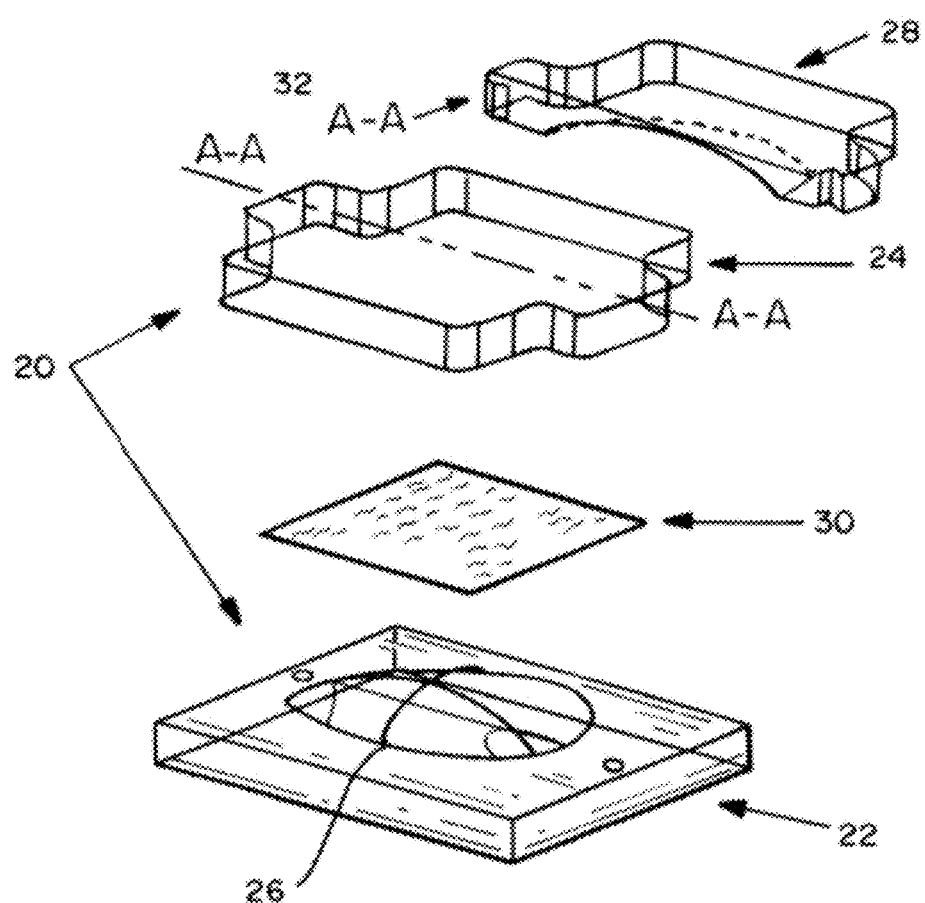
FIG. 3 is a diagram of a split metal form (20), including an inwardly curving half (22) and a mating outwardly curving half (28) with a semicircular groove (26) in the outlying border of the inwardly curving half (22), which is used to make implants that can assume a three-dimensional shape unaided. A line in the outwardly curving half (24) designated by the letters "AA" denotes the position of a cross-section view (32) of the outwardly curving half of the mold (24). A material (30) to be molded is sandwiched in the split metal mold.

B. Method of Forming Implants Including a Support Component and a Shape Memory Component The implants of FIGS. 1 and 2 can be manufactured using a metal form and standard manufacturing techniques. FIG. 3 is a diagram of a split metal form (20), including an inwardly curving half (22) and a mating outwardly curving half (24) with a semicircular groove (26) in the outlying border of the inwardly curving half (22), which is used to make implants that can assume a three-dimensional shape unaided. A line in the outwardly curving half (24) designated by the letters "AA" denotes the position of a cross-section view (32) of the outwardly curving half of the mold (20). A material (30) to be molded is sandwiched in the split metal mold.

Figure 15A:
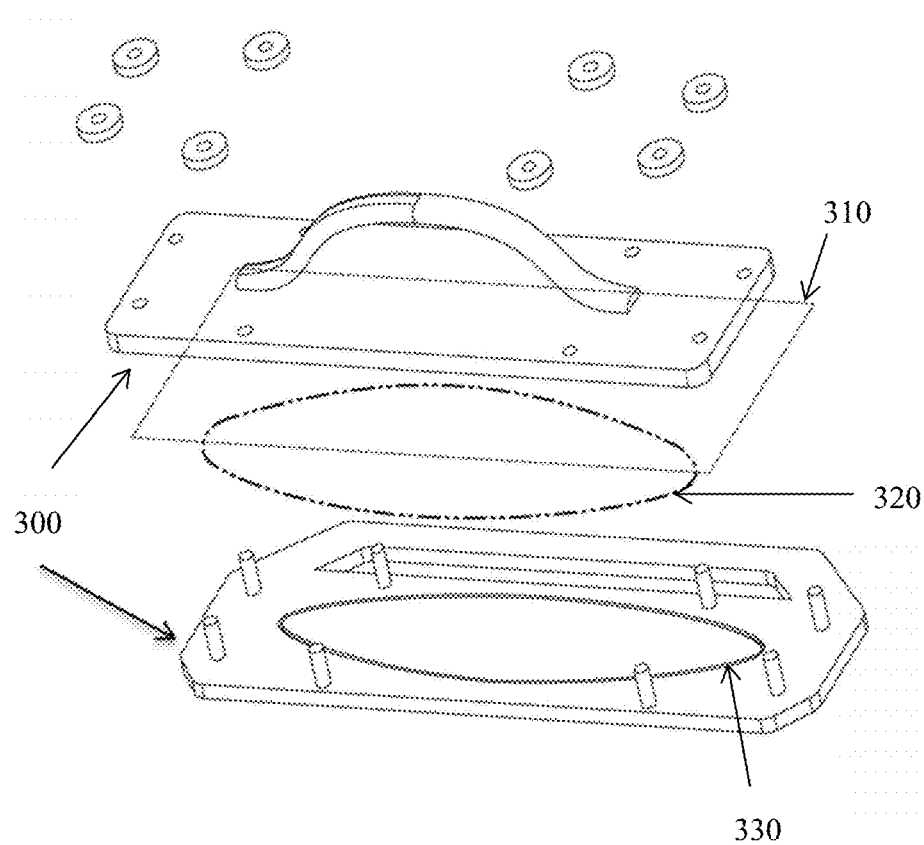
FIG. 15A is a diagram of a split metal form (300) used to attach scaffold material (310) to a ring of extrudate (320). The ring of extrudate is placed in a semicircular groove (330) in one half of the split metal form.
Figure 15B:
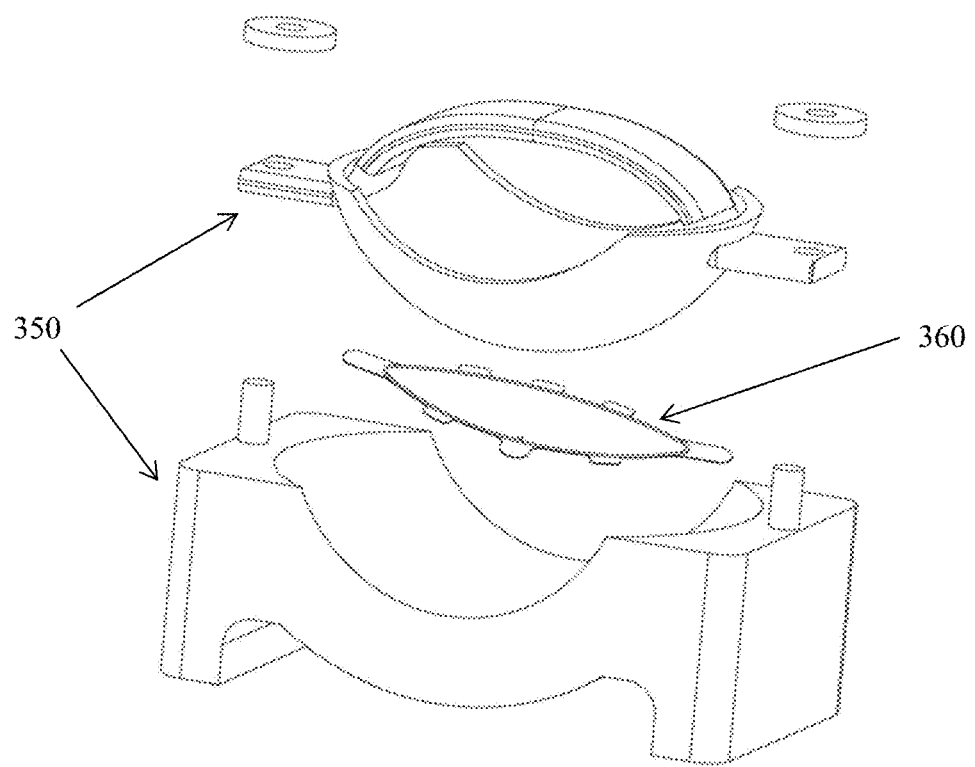
FIG. 15B is a diagram of a split metal form (350) with an inwardly curving half and a mating outwardly curving half, which is used to make implants that can assume a three-dimensional shape unaided. A material (360) to be molded is sandwiched in the split metal mold.
Figure 2:
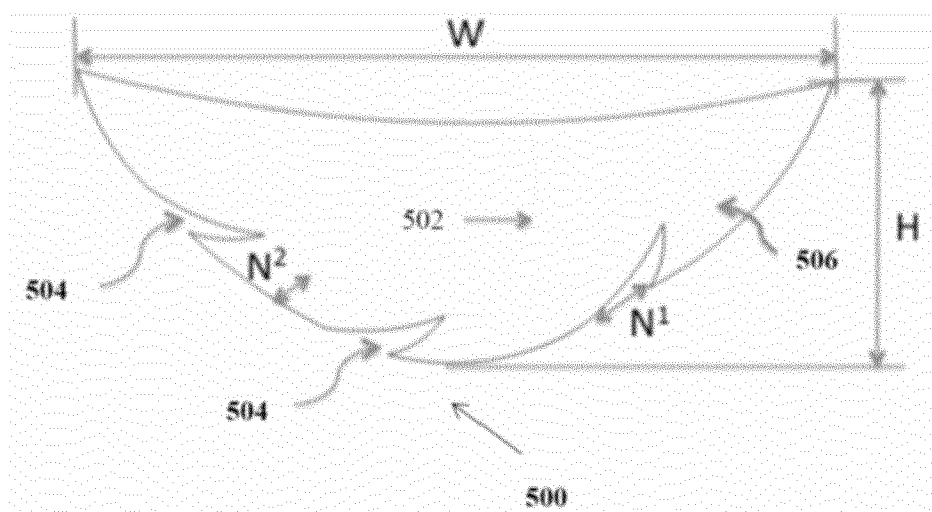

The implants of FIG. 14D can also be manufactured using a metal form and standard manufacturing techniques. FIG. 15A is a diagram of a split metal form (300) that incorporates a semicircular groove in one half of the mold that can be used to attach ribbing (320) to a scaffold material (310). FIG. 15B is a diagram of a second split metal form (350) that can be used to make implants that can assume a three-dimensional shape unaided from the molded forms (360) of ribbing attached to scaffold material. In a preferred embodiment, the implants shown in FIG. 14D have rounded edges (206) to reduce stress in the implants, reduce palpability, reduce bunching of the implant and to minimize patient discomfort.

Shapes with outwardly curving exteriors and inwardly curving interiors may, for example, be prepared using a split metal form consisting of an inwardly curving half and a mating outwardly curving half as shown in FIG. 3. One skilled in the art will understand that the size and shape of the split metal form can be varied in order to provide different three-dimensional shapes that can confer shape to a patient's breast. In a preferred embodiment, the inwardly curving half of the metal form contains a semicircular groove in the outlying border that will accommodate a continuous or interrupted ring of filament, thread, strand, string, fiber, yarn, wire, film, tape, tube, fabric, felt, mesh, multifilament or monofilament. In a particularly preferred embodiment the groove will accommodate a monofilament, preferably a monofilament extrudate. The semicircular groove is cut into the outlying border of the inwardly curving half such that the ring of material, for example, a monofilament, will protrude from the groove. In an alternative embodiment, the groove may be cut into the outwardly curving half instead of the inwardly curving half. In still other embodiments, the groove may be cut into both halves of the split metal form. A three-dimensional shape with an inwardly curving interior, outwardly curving exterior, and reinforced outlying border is prepared by placing, for example, a filamentous or other extrudate in the semicircular groove of the inwardly curving half so that it forms a ring, draping a polymeric material such as a monofilament mesh over the inwardly curving half of the metal form, placing the mating outwardly curving half of the metal form over the polymeric material, and clamping the two halves of the split metal form together to form a block. The block is then heated, cooled, disassembled, and the three-dimensional shape removed and trimmed as necessary to form a smooth outlying border. In an embodiment, the block is heated uniformly, preferably by heating with hot water, and cooled uniformly, preferably by cooling with ambient temperature water.

In a preferred embodiment, partial dome shape implants with natural proportions and a better fit to natural breast curves may be prepared by controlling the curvatures (feature 26) of the mold shown in FIG. 3. The curvatures have two radii: a transversal (in transverse plane) curvature radius which may range from 7 to 10 cm and a sagittal (in sagittal plane) curvature radius which may range from 11 to 20 cm. Furthermore, the values of the transversal curvature radius, henceforth referred to as TCR, and the sagittal curvature radius, henceforth referred to as SCR, can preferably be selected such that the ratio TRC/SCR is specifically between 1.5 and 2, and more preferably close to the golden ratio value of 1.61. This specific relationship between TRC and SRC results in a partial dome shape with natural proportions and a better fit to natural breast curves.

In a preferred embodiment, the three-dimensional shape is made from a poly-4-hydroxybutyrate monofilament mesh, and a poly-4-hydroxybutyrate monofilament extrudate. The temperature of the hot water is set such that the ring is either pressed or melted into the outlying border to reinforce the outlying border. When the three-dimensional shape is made from poly-4-hydroxybutyrate, the temperature of the hot water is set at approximately 56° C., and the polymer construct is heated for approximately 5 minutes. We have discovered that provided a ring of polymer, derived, for example, from a poly-4-hydroxybutyrate monofilament extrudate, is used to reinforce the outlying border of the poly-4-hydroxybutyrate scaffold, the scaffold can be temporarily deformed for implantation, and will then resume its three-dimensional shape when released in a suitably dissected tissue plane. However, if a ring/ribbing is not used to reinforce the edge of the poly-4-hydroxybutyrate material (such as a monofilament mesh), the poly-4-hydroxybuyrate material will not be able to resume a three-dimensional shape.

The implants can be cut or trimmed with scissors, blades, other sharp cutting instruments, or thermal knives in order to provide the desired shapes. For example, a custom die can be used to cut the mesh along the fused ribbing. Examples of custom dies that can be used create up to 17 tabs are shown in FIGS. 14A (3 tabs), 14B (8 tabs) and 14C (17 tabs). The implants can also be cut into the desired shapes using laser-cutting techniques. This can be particularly advantageous in shaping fiber-based implants because the technique is versatile, and importantly can provide shaped products with sealed edges that do not shed cut loops or debris produced in the cutting process.

III. Methods of Implanting

The implants are most suited to use in mastopexy or mastopexy augmentation procedures, wherein the skin of the lower pole is dissected away from the breast and eventually tightened to provide a more appealing breast contour. However, the implants may also be used in other procedures such as revision procedures following the removal of a breast implant, and breast reconstruction procedures following mastectomy, particularly where it is desirable to retain the position of a silicone or saline breast implant or tissue expander. For example, the implants may be used on the lateral side of a patient's breast to properly retain a breast implant, or to cover a breast implant. The implants may also be used in conjunction with expanders in breast reconstruction procedures to give additional support for the skin surrounding an expander, and to create a pocket for a breast implant. They may also be implanted to cover any defects in the major pectoralis muscle, after insertion of breast implants, in patients undergoing breast reconstruction where the muscle has been compromised as a result of breast cancer and mastectomy.

Any current mastopexy technique may be used to achieve a breast lift with the implants using any appropriate skin resection pattern, provided it preserves the functional integrity of the mammary structures. The implants can also be implanted using minimally invasive techniques such as those disclosed by U.S. Patent Application No. 20120283826 to Moses et al.

The chosen method will depend upon the extent of breast ptosis and a number of other factors. The four main techniques for mastopexy are the: crescent mastopexy, donut (or Benelli) mastopexy, lollipop (or vertical) mastopexy, and anchor (or Weiss or Wise) mastopexy. In the crescent mastopexy, a semi-circular incision is made on the upper side of the areolar, and a crescent shaped piece of breast tissue removed. This procedure is typically used for patients with only mild ptosis where a good lift can be achieved by removing excess skin on the upper breast, and suturing the skin back in order to elevate the areolar nipple complex. In one embodiment, the implants can be implanted after further dissection and/or resection to provide additional support for the upper breast tissue.

The implants can also be implanted during a donut or Benelli mastopexy. In this procedure, a donut shaped piece of breast skin is removed from around the areolar with an inner incision line following the perimeter of the areolar, and an outer incision line circling the areolar further out. In one embodiment, the implant(s) can be inserted after further dissection to support the lift, and a purse string suture used to approximate the breast skin back to the areolar.

In both the lollipop and anchor mastopexy procedures, incisions are made around the areolar complex. In the lollipop procedure, a vertical incision is made in the lower breast from the areolar to the inframammary fold, and in the anchor mastopexy procedure an incision is made across the inframammary fold in addition to the vertical incision used in the lollipop procedure. The lollipop procedure is generally used for patients with moderate ptosis, whereas the anchor procedure is normally reserved for patients with more severe ptosis. These two procedures can be performed with or without breast implant augmentation. In both procedures, breast tissue may be resected, and the resected edges sutured together to create a lift. Prior to suturing the resected tissue, the implants can be implanted to support the breast, and to decrease the forces on the resected skin and suture line after closure. In a particularly preferred procedure, the implants are positioned to support the breast parenchyma or implant, and to minimize the weight of the breast on the skin and suture line. In an even more preferred procedure, the suture line is closed with minimal or no tension on the wound to minimize scar formation.

In a preferred embodiment, when sutured in place, the implants provide support, elevation and shape to the breast by anchoring of the implants at one or more locations to the tissue, muscle, fascia or the bones of the chest or torso. In a particularly preferred embodiment, the implants are sutured to the pectoralis fascia or the clavicle. The implants may also be sutured to the chest wall or fascia, and in a particularly preferred embodiment, the implants may be sutured to the chest wall so that they provide slings for support of the lifted breast or breast implant.

The teardrop implant of FIG. 1 is designed to be implanted with the wider section positioned medially for primary load support, and the tapered section positioned on the side of the chest near the arm for lateral support and to direct the breast to the cleavage area. Thus in a preferred embodiment, the implant is asymmetric, and has a precise geometric form. The implant may be anchored first in the medial position using the two suture tabs located in the wider section of the implant, and then the tapered end of the implant subsequently anchored, preferably under tension. Tabs are shown in FIG. 1 having a length to width ratio ranging from about 1:1 to 1:2. However, the shape and size of the tabs may vary widely and are only intended to be limited as recited in the appended claims.

In a preferred embodiment, the three-dimensional implants with shape memory are implanted using minimally invasive techniques into a suitably dissected tissue plane to confer shape to the breast. These implants may, for example, be rolled up into a small cylindrical shape, placed inside a tubular inserter, and implanted through a small incision, such as a standard size incision at the inframammary fold that is usually used for breast augmentation. Once released in vivo, these implants will resume their original three-dimensional shapes, and may be moved into position, for example, to confer shape to the host's breast tissue or an anatomical shape of the breast. In one preferred embodiment, the implant is delivered by employing an IMF incision used as the entry point for dissection, along with a periareolar incision, in a mastopexy procedure. Once skin removal and dissection is complete, a three-dimensional shape memory implant can be deployed in vivo and allowed to resume its preformed three-dimensional shape. The relative rigidity of the self-reinforcing three-dimensional implant allows the implant to remain in place. One skilled in the art will appreciate that these three-dimensional implants can also be delivered by other minimally invasive methods as well as using more traditional open surgery techniques.

The present invention will be further understood by reference to the following non-limiting examples.

Example 1: Regeneration of Tissue from a Bicomponent P4HB Implant

Materials and Methods

A bicomponent P4HB absorbable implant was prepared from a thin 60 µm thick extruded film of P4HB and a knitted P4HB monofilament construct with average pore diameter of approx. 500 µm and an areal density of approx. 182 g/m$^2$. The film was bonded to the mesh by ultrasonically welding the layers together using small pieces of P4HB extrudate (approx. OD 1.5 mm, length 1.27 mm) as a binder. The welding was performed using a model 2000X Branson ultrasonic welder with a 5×5 inch horn and a flat metal anvil. The knitted construct was placed on the anvil and pieces of the extrudate were placed on the knitted material at a spacing of about 13 to 19 mm. The film was then positioned so that the pieces of extrudate were between the film and knitted materials. The horn was lowered and the layers were welded together with a burst of ultrasonic energy (weld energy 100 J, 0.5 s, amplitude 90% fixed, 0.21 MPa pressure). The molecular weights (Mw) of the film and knitted materials relative to polystyrene were 313 kDa and 305 kDa, respectively.

Six samples of the P4HB implant (51×51 mm) were implanted subcutaneously in the backs of New Zealand white rabbits. A total of 17 rabbits were implanted; three rabbits for 4, 12 and 26 weeks, and four rabbits for 52 and 78 weeks. Following explanation, one explant from each rabbit was kept for histological analysis and the remaining explants (n=5 per animal) were used for mechanical and molecular weight testing. A total of 15 samples were received and analyzed for the 4, 12, 26 and 78-week time points, while 20 samples were received and analyzed at 52 weeks. The mechanical testing data is summarized in Table 1.

Results

The bicomponent implant had a thickness of 0.613 mm, and the knitted structure had an average pore diameter of approx. 500 µm. The burst pressure of the implant was approximately 3.09 MPa.

As noted in Table 1, a portion of the 52 and 78-week explants were tested as received and were observed to have higher than expected burst values (i.e. the average burst value at 52 weeks is higher than the 26 week value, while the value at 78 weeks is similar to that at 26 weeks). This is the result of the presence of in-grown, attached tissue adding to the bursting pressure of the combined tissue/P4HB explant. When the remaining explants at 52 weeks were treated with collagenase (noted as "enzyme" in Table 1) to remove the ingrown, attached tissue, many samples of the P4HB implant were found to have degraded significantly and were unsuitable for mechanical testing (n=9). The average burst pressure value (0.17 MPa) of these intact samples (n=5) remaining at 52 weeks after enzyme digestion is recorded in Table 1. After 78 weeks, none of the enzymatically digested samples were suitable for mechanical testing so burst pressure at 78 weeks was only recorded for as received samples (i.e. without enzyme digestion). It should be noted that the 4, 12 and 26-week explants were only tested as received (i.e. without enzyme digestion), and that the P4HB film became rapidly porous and was quickly degraded.

The data in Table 1 demonstrate that the P4HB implant is replaced in vivo by regenerated host tissue with a significant burst pressure that is more than sufficient to support a reconstructed breast. At 78 weeks, the average burst pressure of the as received explants was 0.98 MPa, while the enzymatically digested explants demonstrated that the original P4HB implant did not contribute to the burst pressure and was substantially degraded. At 52 weeks, the P4HB implant was also found to be significantly degraded with the enzymatically degraded P4HB implant having a residual burst pressure of just 0.17 MPa. In contrast, the explants at 52 weeks that had not been enzymatically digested had an average burst pressure of 1.47 MPa. This means that at 52 weeks, the majority of the burst pressure is due to the tissue, rather than the P4HB implant, and at 78 weeks all the burst pressure is due to the regenerated tissue.

TABLE 1

Properties of Implant over Time after Digestion

| Implant Time (wks) | # Tested (n) | Burst Pressure MPa | % Strength Retention |
|---|---|---|---|
| 0 | 4 | 3.08 | 100 |
| 4 | 15 | 2.37 | 77 |
| 12 | 15 | 1.39 | 45 |
| 26 | 15 | 1.11 | 36 |
| 52 enzyme digested | 5 | 0.17 | 5 |
| 52 as received | 6 | 1.47 | 48 |
| 78 enzyme digested | 6 | 0 | ND |
| 78 as received | 9 | 0.98 | 32 |

Example 2: Regeneration of Tissue from a P4HB Implant of Thermally Bonded Fibers Materials and Methods A P4HB implant was prepared from thermally bonded fibers of P4HB with a thickness of approximately 1 mm, an areal density of 260 g/m², and a weight average molecular weight relative to polystyrene of 129 kDa. The burst pressure of the P4HB implant was 0.91 MPa, and the pore size of the implant was approximately 50 µm.

Results

The P4HB implants were implanted subcutaneously in the backs of New Zealand white rabbits for 2, 4, 8, 12 and 24 weeks. The ability of the P4HB implants to regenerate host tissue with significant burst pressure was determined. The mechanical testing and molecular weight data for the explants are summarized in Table 2. In contrast to Example 1, none of the explanted samples were enzymatically digested with collagenase for mechanical testing because the thermally bonded fibers of the P4HB implant were found to degrade very rapidly. As shown in Table 2, no recoverable P4HB polymer could be found at the 26-week time point, and therefore the molecular weight of the polymer could not be determined at this time point. All the values shown in Table 2 are for the burst pressure of the as received explants, and are therefore composite values of the residual P4HB implant and the ingrown tissue.

As shown in Table 2, the burst pressure of the explanted samples initially decreased during the first 8 weeks, but then began to increase until the burst pressure reached approx. 0.96 MPa at 26 weeks. This data shows that the P4HB implant can be replaced by regenerated host tissue in vivo, and that the new tissue would be able to support a significant load in a reconstructed breast.

TABLE 2

Properties of Implant over Time

| Time (wk) | Mw (kDa) | Burst Pressure MPa | % Strength Retention |
|---|---|---|---|
| 0 | 129 | 0.91 | 100 |
| 2 | 123 | 0.69 | 76 |
| 4 | 111 | 0.65 | 72 |
| 8 | 95 | 0.43 | 47 |
| 12 | 83 | 0.46 | 50 |
| 26 | NA | 0.96 | 105 |

Example 3: Preparation of an Asymmetric Shaped P4HB Implant

A teardrop shaped P4HB implant having the dimensions and shape shown in FIG. 1 was prepared from a knitted P4HB monofilament structure with a pore diameter of approximately 500 µm, thickness of 0.5 mm, areal density of approx. 182 g/m², suture pullout strength of 5.6 kgf, and a burst pressure of 3.06 MPa. The implant was cut to the desired shape with scissors.

Example 4: Minimally Invasive Delivery of a Two-Dimensional P4HB Implant Minimizing Buckling and Bunching of the Implant Upon Placement A minimally invasive dissection was performed on a cadaver wherein two small (2 inch) incisions were created in standard entry points: a periareolar incision and an inframammary fold incision. This was followed by blunt dissection separating the breast parenchyma from the skin to create a tissue plane from the medial to the lateral sides of the lower pole of the breast. A two-dimensional shaped implant was rolled into a small diameter cylinder, and placed inside an insertion device suitable for deployment of the implant in vivo. The implant was deployed from the insertion device, and placed to confer shape to a breast with minimal buckling and bunching of the implant.

Example 5: Preparation of a P4HB Implant Comprising a Three-Dimensional Scaffold Designed to Confer Shape to a Breast, or Anatomical Shape of a Breast, Wherein the Three-Dimensional Shape can be Temporarily Deformed to Allow for Implantation, and Resume its Three-Dimensional Shape after Implantation A split metal mold consisting of an inwardly curving half and a mating outwardly curving half was prepared, with a semicircular groove placed in the outlying border of the inwardly curving half, as shown in FIG. 3. A P4HB monofilament extrudate was cut to length, and pushed into the semicircular groove with part of the monofilament protruding from the groove. A knitted P4HB monofilament mesh, measuring approx. 15×20 cm, with a pore diameter of approximately 500 µm, thickness of 0.5 mm, areal density of approx. 182 g/m², suture pullout strength of 5.6 kgf, and a burst pressure of 3.06 MPa, was draped over the entire surface of the inwardly curving half of the metal form and the monofilament in the semicircular groove. The mating outwardly curving metal form was gently placed over the mesh, and the two halves of the split metal mold were clamped together to form a block. The block was uniformly heated on all sides by placing the block in hot water maintained at 56° C. for 5 minutes. The block was then uniformly cooled for 1 to 2 minutes by placing the block into a water bath at ambient temperature. The block was disassembled, and the mesh shape gently lifted from the metal mold. Unwanted compressed extrudate was removed from the implant by trimming the outlying border.

Comparative Example 5: Preparation of a P4HB Implant from a Scaffold with a Three-Dimensional Shape without a Reinforced Outlying Border A split metal mold consisting of an inwardly curving half and a mating outwardly curving half was prepared, but without a semicircular groove placed in the outlying border of the inwardly curving half (as described in Example 4). A knitted P4HB monofilament mesh, measuring approx. 15×20 cm, with a pore diameter of approximately 500 µm, thickness of 0.5 mm, areal density of approx. 182 g/m², suture pullout strength of 5.6 kgf, and a burst pressure of 3.06 MPa, was draped over the entire surface of the inwardly curving half of the metal form. The mating outwardly curving metal form was gently placed over the mesh, and the two halves of the split metal mold were clamped together to form a block. The block was uniformly heated on all sides by placing the block in hot water maintained at 56° C. for 5 minutes. The block was then uniformly cooled for 1 to 2 minutes by placing the block into a water bath at ambient temperature. The block was disassembled, and the three-dimensional mesh gently lifted from the metal mold. Unwanted mesh was removed from the implant by trimming.

Example 6: Minimally Invasive Delivery of a Three-Dimensional P4HB Implant with a Reinforced Outlying Border The implant prepared in Example 5 (and with a reinforced outlying border) was rolled into a small diameter cylinder, and placed inside an insertion device suitable for deployment of the implant in vivo. The implant assumed its original three-dimensional shape when the implant was deployed from the insertion device.

Comparative Example 6: Attempted Minimally Invasive Delivery of a Three-Dimensional P4HB Implant without a Reinforced Outlying Border The implant without a reinforced outlying border prepared in Comparative Example 5 was rolled into a small diameter cylinder, and placed inside an insertion device suitable for deployment of the implant in vivo. The implant failed to assume its three-dimensional shape unaided when the implant was deployed from the insertion device. This example demonstrates the need to self-reinforce the outlying border of a P4HB implant in order for the implant to have shape memory and be able to confer shape to a breast.

Example 7: Preparation of a P4HB Implant with a Preformed Three-Dimensional Shape and Tabs, and a Shape Memory Component with Rounded Edges The three-dimensional partial dome implant shown in FIG. 14D was prepared using a two-step molding process. The split metal mold used in the first molding step is shown in FIG. 15A, and consists of two flat surfaces (300) that are used to fuse a flat mesh (310) to a ring of extrudate (320). The split metal mold (300) was used to fuse a P4HB extrudate ribbing to a P4HB monofilament mesh in a flat configuration by cutting a length of P4HB extrudate, and placing it in the semicircular groove (330) of the mold such that part of the monofilament extrudate protrudes from the groove. The diameter of the extrudate used was approximately 1.6 mm. A knitted P4HB monofilament mesh, measuring up to 15×30 cm, with a pore diameter of approximately 500 µm, thickness of 0.5 mm, areal density of approx. 182 g/m², suture pullout strength of 5.6 kgf, and a burst pressure of 3.06 MPa, was draped over the entire surface of the lower half of the first step mold metal form and the P4HB monofilament extrudate in the semicircular groove. The top half of the first step mold was then placed over the mesh to trap the extrudate, and fastened to apply uniform tension. The assembly was uniformly heated on all sides by placing the block in hot water maintained at 57° C. for 5 minutes. The block was then uniformly cooled for 1 to 2 minutes by placing the block into a water bath at ambient temperature. The top half of the first step mold was removed to retrieve the enclosed mesh with fused ribbing in a flat configuration. Tabs were formed in the molded form and unwanted compressed extrudate was removed from the molded form by trimming the outlying border. The molded form was trimmed along the fused ribbing using the custom die shown in FIG. 14B to produce the shape (360) shown in FIG. 15B. (Custom dies were used to form tabs with widths ranging from 1 cm to 3 cm and tab lengths from 2 to 4 cm. In other examples, custom dies such as those shown in FIGS. 14B and 14C, were used to create different numbers of tabs.). In the second molding step, the molded and cut shape form (360) was placed in the split metal mold (350) shown in FIG. 15B with an inwardly curving half and a mating outwardly curving half. The two halves of the second step mold were clamped together to form a block and force the flat mesh into its final three-dimensional configuration. The block was placed in hot water at 49° C. for 1 minute. The assembly was then cooled down and disassembled, and the three-dimensional implant (shown in FIG. 14D) removed from the mold.

The manufacturing procedure described herein was used to make three-dimensional partial dome shape implants as shown in FIG. 14D in three sizes to give surgeons the flexibility to cover a wide range of breast sizes. The dimensions of the two semicircular grooves (330) in FIG. 15A, and the custom cutting dies (examples shown in FIGS. 14A-C), may be readily changed in order to produce different sized implants. The dimensions of the semicircular grooves were selected such that the resulting width shown in FIG. 14D as the ML-distance (208) of the implant was approximately 16.5, 19, and 21 cm and the height (shown in FIG. 14D as the IMF-NAC distance (210)) was approximately 5.5, 6.5, and 7.5 cm respectively. Furthermore, in order to reduce stress concentrations, the implants were prepared with rounded edges (see 206 in FIG. 14D), wherein the radii of the rounded edges ranged from 6 to 10 mm. The rounded edges further serve to reduce palpability, bunching of the implant and to minimize patient discomfort.

Orientation marks to assist in correct placement of the implant during surgery could also be incorporated into the implants during the manufacture of the implants by using a split metal form similar to that shown in FIG. 15A, but also incorporating an additional 5 mm long transversal groove in the semicircular groove (330) of FIG. 15A. A transversal groove in the semicircular groove (330) was used to form orientation mark (202) shown in FIG. 14D.

Modifications and variations of the methods and compositions will be apparent from the foregoing detailed description and are intended to come within the scope of the appended claims.

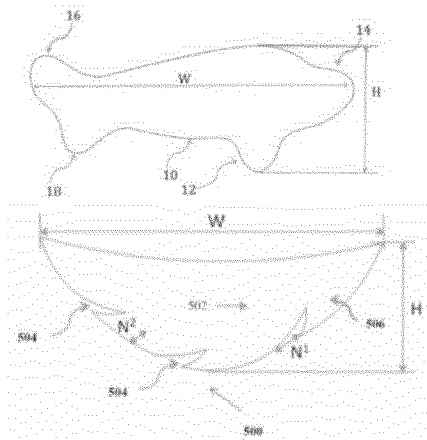

We claim:

1. An implant for breast reconstruction or plastic surgery comprising a porous biodegradable scaffold, wherein the scaffold is prepared from a monofilament fiber made from a synthetic or biological polyester, wherein the scaffold can withstand a load of at least 5 N, more preferably at least 15 N, and even more preferably of at least 60 N.

2. The implant of claim 1, wherein the implant has a three-dimensional shape that substantially represents the shape of the lower pole of the breast.

3. The implant of claim 1, wherein the implant can extend up to 30% in one direction.

4. The implant of claim 1, wherein the porous scaffold has a pore size of at least 10 μm.

5. The implant of claim 1, wherein the scaffold can support a pressure of at least 0.1 kPa.

6. The implant of claim 1, wherein the implant further comprises one or more bioactive agents, coatings including collagen and hyaluronic acid and derivative thereof, additives, and therapeutic, prophylactic or diagnostic agents, including antibiotics, antimicrobial agents, anti-inflammatory agents, radiopaque markers, and contrast agents.

7. The implant of claim 1, wherein the scaffold comprises a monofilament mesh.

8. The implant of claim 1, wherein the scaffold has a suture pullout strength greater than 10 N, and more preferably 20 N.

9. The implant of claim 1, wherein the scaffold has an areal density of 5-800 g/m$^2$.

10. The implant of claim 1, wherein the implant retains at least 20% of its initial burst strength 12 weeks after implantation.

11. The implant of claim 1, wherein the implant further comprises retainers, such as barbs and tacks.

12. The breast implant of claim 1, wherein the breast implant is a silicone or saline implant.

13. The implant of claim 1, wherein the implant further comprises tabs.

14. The implant of claim 1, wherein the implant is suitable for use in conjunction with a tissue expander.

15. The implant of claim 1, wherein the polyester is a polyhydroxyalkanoate.

16. The implant of claim 15, wherein the polyhydroxyalkanoate is poly-4-hydroxybutyrate or copolymer thereof.

17. The implant of claim 1, wherein the polyester comprises one or more of the following monomers: glycolic acid, glycolide, lactic acid, lactide, 1,4-dioxanone, trimethylene carbonate, 3-hydroxybutyric acid, and ε-caprolactone.

18. A breast reconstruction method comprising administration a breast implant at the site in need thereof, and the scaffold of claim 1.

19. The method of claim 18, comprising creating a pocket a pocket for the breast implant using the scaffold.

20. The method of claim 18 wherein the site comprises the major pectoralis muscle.

* * * * *

UNITED STATES PATENT AND TRADEMARK OFFICE
CERTIFICATE OF CORRECTION

PATENT NO. : 10,058,417 B2
APPLICATION NO. : 15/489330
DATED : August 28, 2018
INVENTOR(S) : Skander Limem et al.

Page 1 of 4

It is certified that error appears in the above-identified patent and that said Letters Patent is hereby corrected as shown below:

On the Title Page

Delete the title page and substitute therefore with the attached title page consisting of the corrected illustrative figure(s).

In the Drawings

Sheet 1, FIG. 2, the reference numeral 504 at the bottom of the drawing should be replaced with reference numeral 500 as shown on the attached drawing sheet.

In the Specification

Column 6, Line 36, replace "implant (90)" with --implant--.
Column 14, Line 67, replace "10-11 cm as" with --10-11 cm--.
Column 15, Line 24, replace "mid-body support (90)" with --mid-body support (502)--.
Column 15, Line 25, replace "cut notches (92)" with --cut notches (504)--.
Column 15, Lines 25-26, replace "tabs (94)" with --tabs (506)--.
Column 15, Line 42, replace "the lower region (or tab) (46)" with --the lower region (or tab) (42)--.
Column 15, Line 46, replace "dashed line in FIG. 7" with --dashed line in FIG. 5--.
Column 16, Line 39, replace "implant (900)" with --implant--.
Column 17, Lines 23-24, replace "the highest point (64) shown in FIG. 8D" with --the highest point (94) shown in FIG. 11D--.
Column 17, Line 25, replace "the depth (D) of the dome shown in FIG. 8D" with --the depth (D) of the dome shown in FIG. 11D--.
Column 17, Line 26, replace "angle θ shown in FIG. 8D" with --angle θ shown in FIG. 11D--.
Column 20, Lines 9-10, replace "a support component materials" with --support component materials--.
Column 24, Line 20, replace "that can be used create up to 17 tabs" with --that can be used to create up to 17 tabs--.

Signed and Sealed this
Ninth Day of June, 2020

Andrei Iancu
*Director of the United States Patent and Trademark Office*

In the Claims

Claim 12, Column 32, Line 15, replace "breast implant of claim 1" with --implant of claim 1--.
Claim 12, Column 32, Lines 15-16, replace "the breast implant" with --the implant--.
Claim 18, Column 32, Lines 29-30, replace "administration a breast implant" with --administering a breast implant--.
Claim 19, Column 32, Lines 32-33, replace "a pocket a pocket" with --a pocket--.

(12) United States Patent
Limem et al.

(10) Patent No.: US 10,058,417 B2
(45) Date of Patent: *Aug. 28, 2018

(54) ABSORBABLE IMPLANTS FOR PLASTIC SURGERY

(71) Applicant: Tepha, Inc., Lexington, MA (US)

(72) Inventors: Skander Limem, Melrose, MA (US); Emily Stires, Cambridge, MA (US); Rebecca Holmes, North Reading, MA (US); Said Rizk, Windham, NH (US); Arikha Moses, New York, NY (US); Fabio Felix, Foxborough, MA (US); Bruce Van Natta, Westfield, IN (US); Antonio Fosco, North Reading, MA (US); David P. Martin, Arlington, MA (US); Simon F. Williams, Cambridge, MA (US)

(73) Assignee: Tepha, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/489,330

(22) Filed: Apr. 17, 2017

(65) Prior Publication Data
US 2017/0216018 A1 Aug. 3, 2017

Related U.S. Application Data

(63) Continuation of application No. 14/694,681, filed on Apr. 23, 2015, now Pat. No. 9,655,715, which is a (Continued)

(51) Int. Cl.
A61F 2/12 (2006.01)
A61F 2/00 (2006.01)
(Continued)

(52) U.S. Cl.
CPC .............. *A61F 2/12* (2013.01); *A61F 2/0063* (2013.01); *A61F 2210/0004* (2013.01);
(Continued)

(58) Field of Classification Search
CPC .................................................... A61F 2/12
(Continued)

(56) References Cited

U.S. PATENT DOCUMENTS 4,801,299 A * 1/1989 Brendel .............. A61L 27/3633
128/DIG. 8
5,011,494 A * 4/1991 von Recum .......... A61F 2/0077
600/36
(Continued)

FOREIGN PATENT DOCUMENTS

WO 2004096098 11/2004
WO 2006117622 11/2006
(Continued)

OTHER PUBLICATIONS

Auclair and Mitz, "Repair of mammary ptosis by insertion of an internal absorbable support and periareolar scar", Ann. Chir. Plast. Esthet. 38:107-13 (1993).
(Continued)

Primary Examiner — Suzette J Gherbi
(74) Attorney, Agent, or Firm — Pabst Patent Group LLP

(57) ABSTRACT

Absorbable implants for breast surgery that conform to the breast parenchyma and surrounding chest wall have been developed. These implants support newly lifted breast parenchyma, and/or a breast implant. The implants have mechanical properties sufficient to support a reconstructed breast, and allow the in-growth of tissue into the implant as it degrades. The implants have a strength retention profile allowing the support of the breast to be transitioned from the implant to regenerated host tissue, without significant loss of
(Continued)